(12) United States Patent
Woodard

(10) Patent No.: US 9,615,816 B2
(45) Date of Patent: Apr. 11, 2017

(54) DRIVERS AND DRIVE SYSTEMS

(71) Applicant: Vidacare LLC, Shavano Park, TX (US)

(72) Inventor: Steven Paul Woodard, Cupertino, CA (US)

(73) Assignee: Vidacare LLC, Wayne, PA (US)

( * ) Notice: Subject to any disclaimer, the term of this patent is extended or adjusted under 35 U.S.C. 154(b) by 894 days.

(21) Appl. No.: 13/835,624

(22) Filed: Mar. 15, 2013

(65) Prior Publication Data

US 2014/0262408 A1 Sep. 18, 2014

(51) Int. Cl.
*A61B 10/02* (2006.01)
*A61B 17/16* (2006.01)

(52) U.S. Cl.
CPC ........ *A61B 10/025* (2013.01); *A61B 17/1624* (2013.01); *A61B 17/1637* (2013.01)

(58) Field of Classification Search
CPC ............ A61B 17/1624; A61B 17/1622; A61B 17/32002; A61B 17/148; A61B 17/3472; A61B 2017/00398; A61B 10/025; A61B 2010/0258; B23B 45/008; B23B 35/00; B23B 2228/28
USPC .............. 606/79, 80, 96; 173/213, 216, 217; 74/318, 319
See application file for complete search history.

(56) References Cited

U.S. PATENT DOCUMENTS

| | | | |
|---|---|---|---|
| 5,030,222 A * | 7/1991 | Calandruccio | A61B 17/1703 606/79 |
| 5,145,369 A | 9/1992 | Lustig et al. | 433/118 |
| 5,207,697 A | 5/1993 | Carusillo et al. | 606/167 |
| 5,993,454 A * | 11/1999 | Longo | A61B 17/1624 606/80 |
| 6,042,585 A | 3/2000 | Norman | 606/104 |
| 6,110,174 A * | 8/2000 | Nichter | A61B 17/1697 606/103 |
| 6,223,833 B1 * | 5/2001 | Thurler | B25D 16/00 173/109 |
| 7,074,225 B2 * | 7/2006 | Kimura | A61B 17/1622 606/80 |
| 8,757,285 B2 * | 6/2014 | Weber | B24B 23/04 173/216 |
| 2004/0191897 A1 | 9/2004 | Muschler | 435/325 |
| 2007/0282344 A1 * | 12/2007 | Yedlicka | A61B 17/1615 606/80 |
| 2009/0050343 A1 * | 2/2009 | Smith | A61B 17/1624 173/216 |

FOREIGN PATENT DOCUMENTS

| | | |
|---|---|---|
| WO | WO 2008033874 | 3/2008 |
| WO | WO 2011123703 | 10/2011 |

OTHER PUBLICATIONS

International Search Report and Written Opinion issued in PCT/US2014/028594, mailed on Jul. 28, 2014.

* cited by examiner

*Primary Examiner* — Nathaniel Chukwurah
(74) *Attorney, Agent, or Firm* — Baker & Hostetler LLP

(57) ABSTRACT

Drivers and drive systems (e.g., off-axis drive systems, pneumatic motors, multi-gear drive systems, and/or the like), and kits comprising drivers with drive systems, such as those, for example, configured to move a drive shaft.

19 Claims, 25 Drawing Sheets

SECTION B-B

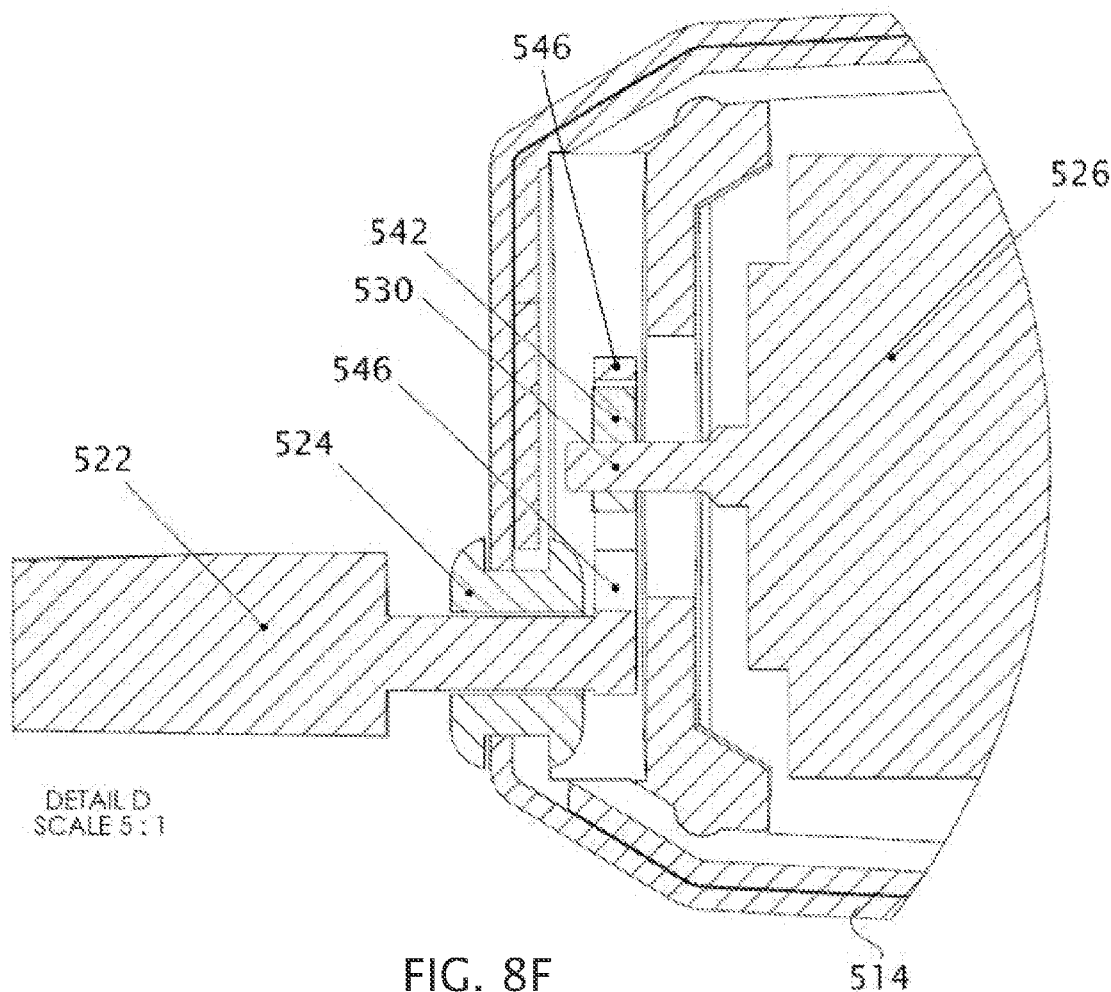

DRIVERS AND DRIVE SYSTEMS

BACKGROUND

1. Field of the Invention

The present invention relates generally to drivers, and more particularly, but not by way of limitation, to drivers with drive systems (e.g., off-axis drive systems, pneumatic motors, multi-gear drive systems, and/or the like) configured to move a drive shaft (e.g., for driving or inserting intraosseous devices and/or devices for obtaining bone marrow samples) and kits comprising such drivers and drive systems.

2. Description of Related Art

Examples of drivers for use with medical devices (e.g., for driving or inserting intraosseous devices and/or devices for obtaining bone marrow samples) are disclosed in (1) U.S. Pat. No. 7,670,328; (2) U.S. Pat. No. 7,699,850; (3) Patent Application Publication No. US 2008/0045965; and (4) Patent Application Publication No. US 2005/0131345.

SUMMARY

This disclosure includes embodiments of drivers, drive systems (e.g., off-axis drive systems, pneumatic motors, multi-gear drive systems, and/or the like), and kits comprising drivers with drive systems configured to move a drive shaft.

Some embodiments of the present drivers comprise a drive shaft configured to be coupled to an intraosseous device; a motor coupled to a power source and further coupled to the drive shaft by a non-geared off-axis drive system; and a trigger coupled to the motor and configured to activate the motor to move the drive shaft, where the non-geared off-axis drive system is configured to cause oscillating rotation of the drive shaft. In some embodiments, the non-geared off-axis drive system comprises: a cam having a centerpoint through which a first axis passes and a bore having a centerpoint through which a second axis that is different from the first axis passes, where at least a portion of the motor is configured to extend through the bore along the second axis such that the motor can rotate the cam about the second axis; and a linking device coupled to the cam and further coupled to the drive shaft, the linking device configured to transfer motion from the cam to the drive shaft.

In some embodiments, the driver can further comprise a driver housing and a bearing coupled to the driver housing, the drive shaft extending through the bearing to permit the drive shaft to move without contacting the housing. In some embodiments, the motor comprises a motor shaft configured to extend through the bore of the cam along the second axis. In some embodiments, the motor shaft is coupled to the cam. In some embodiments, the linking device contacts at least a portion of an outer surface of the cam when the motor rotates the cam. In some embodiments, the linking device contacts at least a portion of an outer surface of the drive shaft when the motor rotates the cam. In some embodiments, the linking device is coupled to the drive shaft such that the drive shaft moves in fixed relation to the portion of the linking device coupled to the drive shaft. In some embodiments, a range of oscillating rotation of the drive shaft is equal to or less than 30 degrees. In some embodiments, the power source comprises a battery.

Some embodiments of the present drivers comprise a drive shaft configured to be coupled to an intraosseous device; a motor coupled to a power source and further coupled to the drive shaft by a multi-gear drive system, where the motor is coupled in fixed relation to at least one gear of the multi-gear drive system; and a trigger coupled to the motor and configured to activate the motor to move the drive shaft, where the multi-gear drive system is configured to cause oscillating rotation of the drive shaft. In some embodiments, the multi-gear drive system comprises a first gear comprising: a first bore, the motor configured to extend through the first bore to rotate the first gear; a first surface extending radially outward from the first bore; a second surface extending radially inward from an outer edge of the first gear; and a third surface between the first and second surfaces and recessed with respect to the first and second surfaces forming an inner wall and an outer wall, where at least a portion of the inner and outer walls comprises a plurality of teeth; and a second gear disposed adjacent to the third surface and between the inner wall and the outer wall, the second gear comprising: a plurality of teeth configured to engage the teeth of the inner and outer walls; and a second bore, the drive shaft configured to extend through the second bore such that the second gear can rotate the drive shaft. In some embodiments, the teeth of the inner wall and the teeth of the outer wall engage the teeth of the second gear at a different time. In some embodiments, the teeth of the inner wall are configured to engage the teeth of the second gear such that the second gear rotates in a different direction than when the teeth of the outer wall engage the teeth of the second gear. In some embodiments, the inner wall is substantially perpendicular to the first and third surfaces. In some embodiments, the outer wall is substantially perpendicular to the second and third surfaces. In some embodiments, the inner wall comprises a first height extending from the third surface to the first surface and the outer wall comprises a second height extending from the third surface to the second surface. In some embodiments, the first height of the inner wall is substantially equal to the second height of the outer wall are substantially the same. In some embodiments, the drive shaft is coupled to the second gear. In some embodiments, the motor is coupled to the first gear. In some embodiments, the motor comprises a motor shaft configured to extend through the first bore of the first gear to rotate the first gear. In some embodiments, the motor shaft is coupled to the first gear. In some embodiments, a range of oscillating rotation of the drive shaft is equal to or less than 30 degrees. In some embodiments, the power source comprises a battery.

Some embodiments of the present drivers comprise a drive shaft configured to be coupled to an intraosseous device; a motor assembly coupled to the drive shaft and configured to move the drive shaft when a gas enters the motor assembly; and a trigger configured to release the gas into the motor assembly when the trigger is engaged. In some embodiments, the motor assembly comprises a rotor housing having a first end, a second end, and an inner wall defining a chamber at least partially between the first end and the second end, the rotor housing having an opening through which the gas can enter the motor assembly; a rotor disposed within the chamber of the rotor housing and coupled to the drive shaft, the rotor having a first end, a second end, and a plurality of radial slots extending at least partially between the first end and the second end; and a plurality of vanes at least partially disposed within the plurality of radial slots and coupled to the rotor, the plurality of vanes configured such that when the gas enters the motor assembly, the gas applies a force to at least a portion of the plurality of vanes to move the rotor. In some embodiments, the plurality of vanes are coupled to the rotor by a spring. In some embodiments, the spring biases each vane of the plurality of vanes away from the rotor. In some embodiments, the rotor housing, the rotor, and the plurality of vanes cooperate to form a plurality of sub-chambers extending longitudinally with respect to the chamber, the plurality of sub-chambers varying in volume to create a pressure gradient when the gas enters the motor assembly. In some embodiments, the plurality of vanes contact the rotor housing to form the plurality of sub-chambers. In some embodiments, the rotor housing comprises an exhaust channel configured to permit the gas to exit the motor assembly. In some embodiments, the rotor is coupled to the drive shaft by a gear assembly configured to increase a torque and decrease a rotational velocity of the drive shaft with respect to the rotor.

Some embodiments of the present drivers comprise a gear assembly comprising an inner gear coupled to the rotor to permit rotor to rotate the inner gear; an outer gear coupled to the drive shaft to permit the outer gear to rotate the drive shaft; and a plurality of planetary gears coupled to the inner gear and outer gear and configured to transfer rotational motion from the inner gear to the outer gear. In some embodiments, the inner gear comprises a first diameter and the outer gear comprises a second diameter and the second diameter is greater than the first diameter. In some embodiments, the inner gear is concentric with the outer gear. In some embodiments, the planetary gears rotate about the inner gear to transfer rotational motion to the outer gear.

Some embodiments of the present drivers further comprise a housing having a handle, the handle having an opening configured to receive a container containing a gas. In some embodiments, the handle is configured to be coupled to the container. In some embodiments, the handle is configured to be threadably coupled to the container. Some embodiments of the present drivers further comprise a container valve configured to release gas from a container into a first passage if a container is coupled to the handle. In some embodiments, the trigger comprises a trigger valve configured to be engaged to release gas from the first passage into a second passage. In some embodiments, when the trigger is engaged, the first passage and the second passage are in fluid communication with the motor assembly. In some embodiments, the gas is a compressed gas (e.g., between 120 to 160 pounds per square inch, between 80 to 120 pounds per square inch, and the like). In some embodiments, the gas comprises air, nitrogen, and/or inert gas. In some embodiments, the motor assembly comprises aluminum, steel, and/or stainless steel. In some embodiments, the rotor is configured to rotate 1 to 5,000 rotations per minute, 5,000 to 25,000 rotations per minute, and/or 25,000 to 50,000 rotations per minute.

Some embodiments of the present drivers comprise an intraosseous device configured to be coupled to the drive shaft. In some embodiments, the intraosseous device comprises a cannula having a cannula first end, a cannula second end, and a cannula bore extending between the cannula first end and the cannula second end, the cannula first end comprising at least one cutting surface configured to penetrate a target area. In some embodiments, the cannula first end comprises a plurality of crowns having at least one cutting surface between adjacent crowns, where the crowns and the cutting surfaces are configured to penetrate the target area. In some embodiments, the cannula further comprises a first hub coupled to the cannula second end and configured to be coupled to the drive shaft. In some embodiments, the first hub comprises a depth limiter configured to limit the depth to which the cannula can penetrate the target area. Some embodiments of the present intraosseous devices comprise a first end having a plurality of tips configured to penetrate a target area, where each tip is formed by an intersection of at least two substantially planar cutting surfaces; a second end configured to be coupled to a driver, the driver configured to rotate the intraosseous device using a compressed gas; and a bore extending between the first end and the second end.

Some embodiments of the present drivers comprise a stylet configured to be disposed in the cannula bore such that a first end of the stylet cooperates with the cannula first end to define a tip for penetrating the target area. In some embodiments, the stylet is configured to be disposed in the cannula such that the first end of the stylet and the cannula first end cooperate to form a cutting surface. In some embodiments, the cutting surface is substantially planar. In some embodiments, the first end of the stylet comprises at least one tip; a first tapered cutting surface extending a first length from the at least one tip; and a second tapered cutting surface extending a second length from the at least one tip, where the first length of the first tapered cutting surface is less than the second length of the second tapered cutting surface.

Some embodiments of the present drivers comprise a second hub coupled to a second end of the stylet and further configured to be releasably coupled to the first hub. In some embodiments, the second hub is configured to be coupled to the first hub by a Luer lock fitting.

Some embodiments of the present drivers comprise a coupler having a first end and a second end, the first end of the coupler configured to be coupled to at least one of the first hub and the second hub, the second end of the coupler configured to be coupled to the drive shaft. In some embodiments, the coupler comprises a depth limiter configured to limit the depth to which at least one of the cannula and the stylet can penetrate the target area.

Some embodiments of the present kits comprise a driver having any of the features previously disclosed and an intraosseous device configured to be coupled to the driver. In some embodiments, the intraosseous device comprises at least one of a cannula and a stylet. In some embodiments, a kit can further comprise a coupler having a first end and a second end, the first end configured to be coupled to the intraosseous device, the second end configured to be coupled to the driver. In some embodiments, a kit can comprise a containment bag configured to receive the driver to prevent desterilization of at least one of the target area, the cannula, and the stylet. In some embodiments, a kit can comprise at least one sharp protector configured such that at least one of the cannula and the stylet can be disposed in the sharp protector to prevent exposure of a cutting surface.

Any embodiment of any of the present drivers, drive systems, and kits can consist of or consist essentially of— rather than comprise/include/contain/have—any of the described elements and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures illustrate the described elements using graphical symbols that will be understood by those of ordinary skill in the art. The embodiments of the present drivers, drive systems, and kits and their components shown in the figures are drawn to scale for at least the embodiments shown.

FIGS. 6A-6C depict various views of the coupler assembly of FIG. 3.

FIG. 8F depicts a side cross-sectional view of a portion of the driver of FIG. 8C.

DESCRIPTION OF ILLUSTRATIVE EMBODIMENTS

Figure 1A:
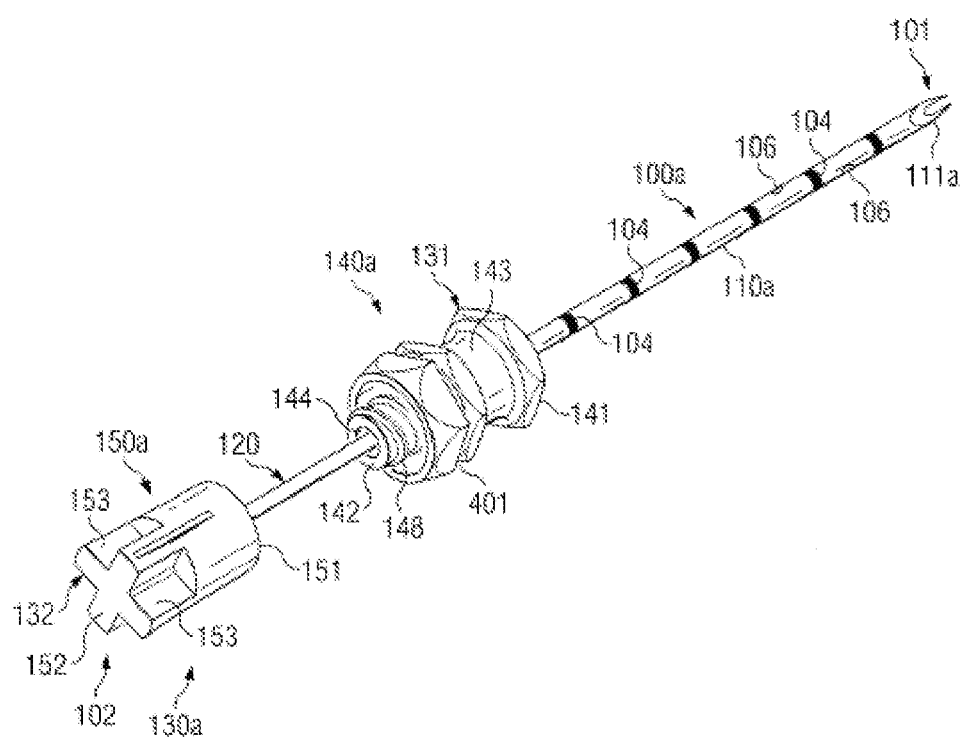
FIG. 1A depicts a perspective view of a prior art intraosseous device having a cannula and a stylet.

The term "coupled" is defined as connected, although not necessarily directly, and not necessarily mechanically. Two items are "couplable" if they can be coupled to each other. Unless the context explicitly requires otherwise, items that are couplable are also decouplable, and vice-versa. One non-limiting way in which a first structure is couplable to a second structure is for the first structure to be configured to be coupled to the second structure. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a driver, drive system, or kit, or a component of a driver, drive system, or kit, that "comprises," "has," "includes" or "contains" one or more elements or features possesses those one or more elements or features, but is not limited to possessing only those elements or features. Likewise, a method that "comprises," "has," "includes" or "contains" one or more steps possesses those one or more steps, but is not limited to possessing only those one or more steps. Additionally, terms such as "first" and "second" are used only to differentiate structures or features, and not to limit the different structures or features to a particular order.

Further, drivers (e.g., with drive systems) and kits comprising such drivers and drive systems configured in a certain way are configured in at least that way, but can also be configured in other ways than those specifically described.

Various types of coupler assemblies incorporating teachings of the present disclosure may be satisfactorily used to releasably engage one end of a shaft extending from a driver with one end of an intraosseous device. For some embodiments, the powered driver may include a driveshaft having one end with a generally hexagonal cross section operable to be releasably engaged with a latch mechanism disposed in one end of a coupler assembly. For some embodiments, a coupler assembly incorporating teachings of the present disclosure may be referred to as a "hands free" coupler, a quick disconnect or quick release coupler and/or port assembly.

Embodiments of the present powered drivers and drive systems may be used to insert an IO device incorporating teachings of the present disclosure into a selected target area or target site in ten seconds or less. However, various teachings of the present disclosure are not limited to use with powered drivers. Manual drivers and spring powered drivers may also be used with IO devices and some embodiments of drive systems incorporating teachings of the present disclosure.

Examples of manual drivers are shown in co-pending patent application Ser. No. 11/042,912 entitled Manual Intraosseous Device filed Jan. 25, 2005 (published as US 2005/0165404). The term "fluid" may be used in this application to include liquids such as, but not limited to, blood, water, saline solutions, IV solutions, plasma, or any mixture of liquids, particulate matter, dissolved medication, and/or drugs associated with biopsy or aspiration of bone marrow or communication of fluids with bone marrow or other target sites. The term "fluid" may also be used in this patent application to include any body fluids and/or liquids containing particulate matter such as bone marrow and/or cells which may be withdrawn from a target area.

The terms "harvest" and "harvesting" may be used in this application to include bone and/or bone marrow biopsy and bone marrow aspiration. Bone and/or bone marrow biopsy (sometimes referred to as "needle biopsy") may be generally described as removing a relatively small piece or specimen of bone and/or bone marrow from a selected target area for biopsy purposes. Bone marrow aspiration (sometimes referred to as "bone marrow sampling") may be generally described as removing larger quantities of bone marrow from a selected target area. Relatively large quantities of bone marrow may be used for diagnostic, transplantation, and/or research purposes. For example some stem cell research techniques may require relatively large quantities of bone marrow.

The term "insertion site" may be used in this application to describe a location on a bone at which an intraosseous device may be inserted or drilled into the bone and associated bone marrow. Insertion sites are generally covered by skin and soft tissue. The term "target area" refers to any location on or within biological material, such as the biological material of a living human being.

The term "intraosseous (IO) device" may be used in this application to include, but is not limited to, any hollow needle, hollow drill bit, penetrator assembly, bone penetrator, catheter, cannula, trocar, stylet, inner penetrator, outer penetrator, IO needle, biopsy needle, aspiration needle, IO needle set, biopsy needle set or aspiration needle set operable to access or provide access to an intraosseous space or interior portions of a bone. Such IO devices may be formed, at least in part, from metal alloys such as 304 stainless steel and other biocompatible materials associated with needles and similar medical devices.

Embodiments of the present drivers and drive systems can be included in medical procedure trays such as those disclosed in International Patent Application No. PCT/US2007/078207 (published as WO 2008/033874).

The devices and components shown in FIGS. 1A to 7C are prior art devices and components, and the following description of them is provided to give the reader context for the types of devices and components that can be used consistently with embodiments of the present drivers, drive systems, and kits.

Referring now to the drawings, and more particularly to FIG. 1A, shown therein and designated by the reference numeral 100 is one embodiment of the present intraosseous (IO) needle sets or aspiration needle sets. Aspiration needle set 100 comprises a hollow outer penetrator or cannula 110a, a corresponding inner penetrator or stylet (or trocar) 120, and a hub assembly 130a. In the embodiment shown, first end 111a of cannula 110a and first end 121 of stylet 120 are operable or configured to penetrate a bone and associated bone marrow. Various features of first end 111a of cannula 110a and first end 121 of stylet 120 are shown in more detail in FIGS. 1B-1D. First end 101 of IO needle set 100 corresponds generally with first end 111a of cannula 110a and first end 121 of stylet 120.

In the embodiment shown, cannula 110a includes a plurality of markings 104 disposed on exterior portions of the cannula. Markings 104 may be referred to as "positioning marks" or "depth indicators," and may be used to indicate the depth of penetration of needle set 100 into a bone and associated bone marrow. In some embodiments, cannula 110a may have a length of approximately sixty (60) millimeters and/or a nominal outside diameter of approximately 0.017 inches (e.g., corresponding generally to the dimensions of a sixteen (16) gauge needle). Cannula 110a and/or stylet 120 may be formed from stainless steel or other suitable biocompatible materials. In some embodiments, markings 104 are spaced at one (1) centimeter intervals on exterior portions of cannula 110a. In some embodiments, one or more side ports 106 may be formed in exterior portions of cannula 110a spaced from first end 111a.

Hub assembly 130a may be configured and/or used to releasably dispose stylet 120 within the longitudinal bore or lumen of cannula 110a. In the embodiment shown, hub assembly 130a includes a first hub 140a and a second hub 150a. A second end of cannula 110a, opposite from first end 111a, may be securely engaged with hub 140a. The second end of stylet 120, opposite from first end 121, may be securely engaged with the first end of hub 150a. As shown in FIG. 1A, cannula 110a may extend longitudinally from first end 141 of hub 140a. Stylet 120 may also extend from the first end of hub 150a. The second end of hub 140a may include a standard Luer lock fitting which may be releasably engaged with a corresponding Luer lock fitting disposed within the first end of second hub 150a. The Luer lock fitting disposed on the second end of hub 140a may be in fluid communication with the bore or passage in cannula 110a, and may be operable to be releasably engaged with a standard syringe type fitting and/or a standard intravenous (IV) connection. In the embodiment shown, hub 150a includes second end 152 that generally corresponds with second end 132 of hub assembly 130a and second end 102 of IO needle set 100. Hub 140a may include first end 141 which may generally correspond with first end 131 of hub assembly 130a. Cannula 110a may extend longitudinally from first end 141 of hub 140a and first end 131 of hub assembly 130.

Figure 6A:
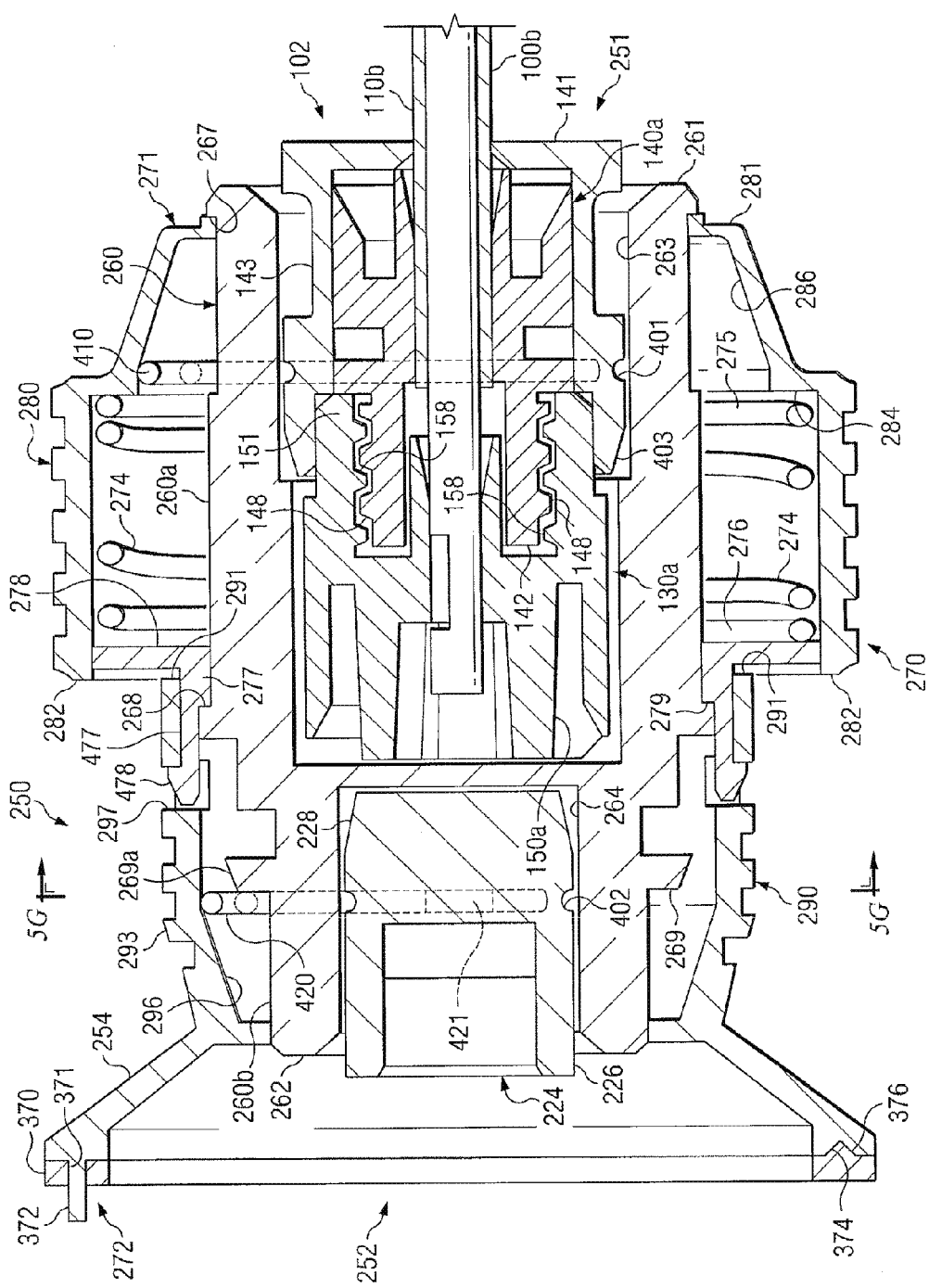
Figure 6B:
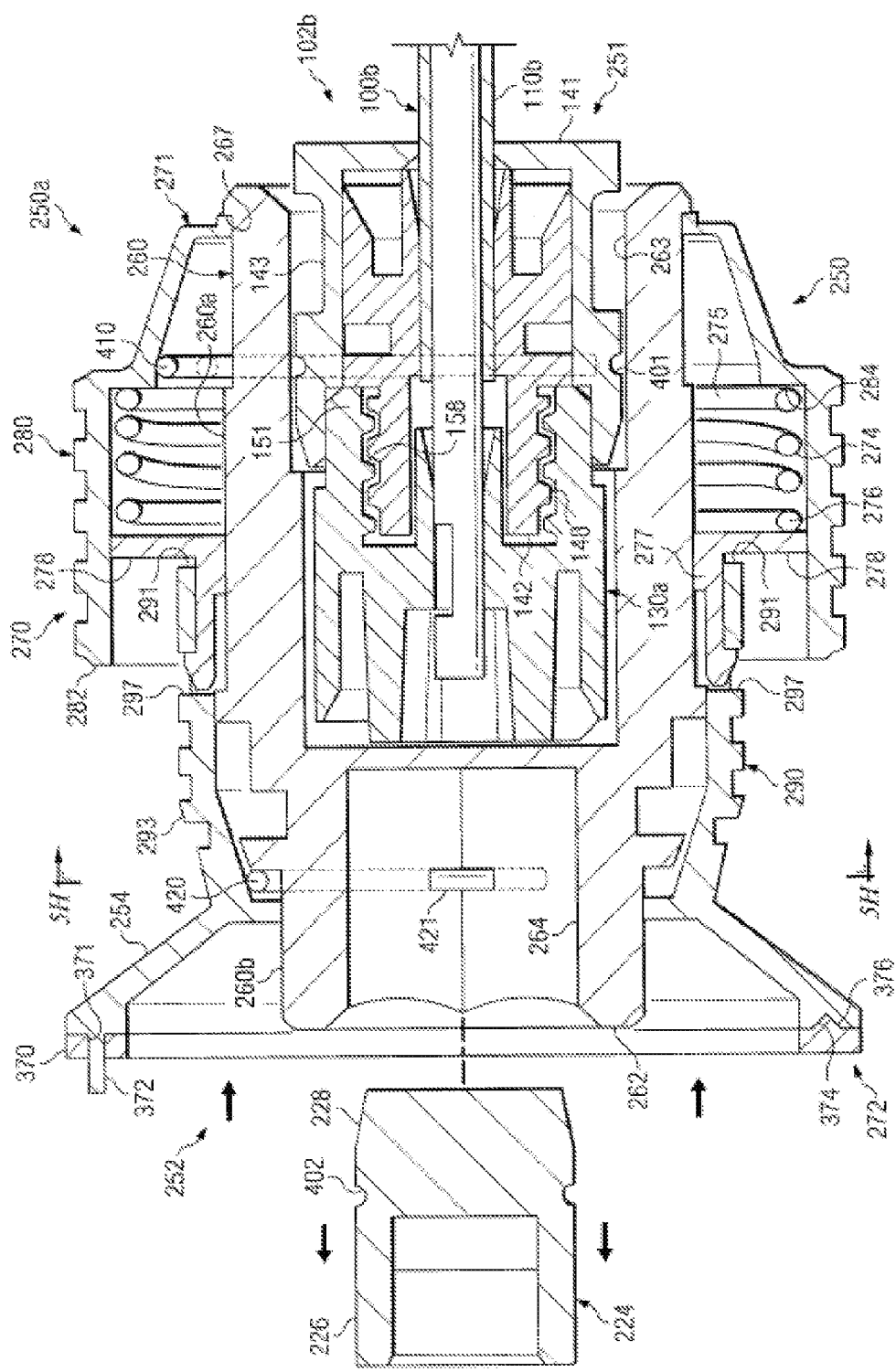

In the embodiment shown, the second end of a hub assembly may be operable to be disposed within a receptacle formed in a coupler assembly, as described in more detail below. One feature of the present disclosure may include forming a hub assembly which may be releasably engaged within a first receptacle disposed in a first end of a coupler assembly (e.g., receptacle 263 proximate first end 261 of elongated core 260 as shown in FIGS. 6A-6B). The dimensions and configuration of receptacle 263 may be selected to prevent rotation of hub 150a relative to hub 140a if hub assembly 130a is disposed in receptacle 263 (e.g., while inserting (rotating) an IO device into a bone and associated bone marrow). A powered driver may be releasably engaged with a second receptacle disposed in a second end of the coupler assembly (e.g., receptacle 264 proximate second end 262 of elongated core 260 as shown in FIGS. 6A-6B).

In the embodiment shown, intraosseous device or aspiration needle set 100a includes first end 151 of hub 150a spaced from second end 142 of hub 140a. Portions of stylet 120 extending from first end 151 of hub 150a are shown slidably disposed within lumen or longitudinal bore 118 of cannula 110a. Hub assembly 130a may include first end 131 which may correspond generally with first end 141 of hub 140a. Hub assembly 130a may also include second end 132 which may correspond generally with second end 152 of hub 150a and second end 102 of hub assembly 130a, as shown. Cannula 110a may be attached to and extend from first end 141 of hub 140a. Second end 142 of hub 140a may include one-half a typical Luer lock connection or fitting operable to be releasably engaged with corresponding portions of a Luer lock connection or fitting disposed in first end 151 of second hub 150a. For embodiments such as the one shown in FIG. 1A, first end 131 of hub assembly 130a may correspond with first end 141 of first hub 140a. Second end 152 of second hub 150a may correspond with second end 132 of hub assembly 130a and second end 102 of aspiration needle set 100a.

At least one portion of hub assembly 130a may have a generally hexagonal cross section operable to be received within the generally hexagonal cross section of receptacle 263 disposed proximate first end 251 of coupler assembly 250, as shown in FIGS. 6A-6B. For some embodiments, portions of first hub 140a disposed adjacent to reduced outside diameter portion 143 may have generally hexagonal cross sections, as shown in FIG. 1A. In other embodiments, various cross sections other than hexagonal may be satisfactorily used to releasably engage a powered driver with one end of a coupler assembly and an intraosseous device with an opposite end of the coupler assembly. Aspiration needle sets may include a trocar, stylet, or penetrator in combination with an associated cannula, catheter or outer penetrator. However, biopsy needles formed in accordance with teachings of the present disclosure may or may not include a trocar, stylet, or inner penetrator.

Hub 140a may include second end 142 with opening 144 formed therein. A passageway may extend from second end 142 towards first end 141 of hub 140a, as illustrated in FIGS. 6A-6B. A passageway may be operable to communicate fluids with lumen 118 of cannula 100a. Second end 142 of hub 140 may include various features of a conventional Luer lock connection or fitting, including threads 148, and corresponding threads 158 may be formed within first end 151 of hub 150a, as shown in FIGS. 6A-6B.

For some applications hub 140a and hub 150a may, for example, be formed using injection molding techniques. For such embodiments hub 140a may include reduced outside diameter portion 143 disposed between first end 141 and second end 142. In a similar manner a plurality of void spaces or cutouts 153 may be formed in hub 150a adjacent to and extending from second end 152 in the direction of first end 151. The configuration and dimensions of reduced diameter portion 143 and/or cutouts 153 may be varied to optimize associated injection molding techniques and at the same time provide required configurations, dimensions and material strength to allow associated hub assembly 130a to function as described in this disclosure.

In some embodiments, tip 123 of stylet 120 may be disposed relatively close to a tip of cannula 110a. For some applications, first end 121 of stylet 120 and first end 111a of cannula 110a may be ground at the same time to form adjacent cutting surfaces. Grinding ends 111a and 121 at the same time may result in forming a single cutting unit to form generally matching cutting edges. Other types of cutting surfaces formed in accordance with teachings of the present disclosure may be discussed later (e.g., as described with reference to FIGS. 1B-1D).

Figure 1B:
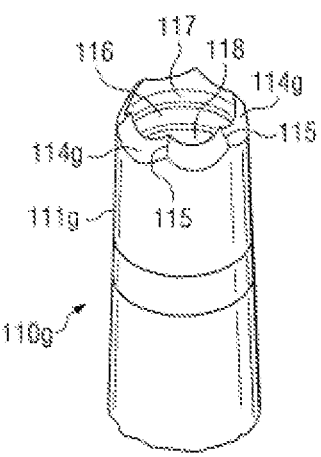
FIG. 1B depicts a perspective view of another prior art cannula.
Figure 1C:
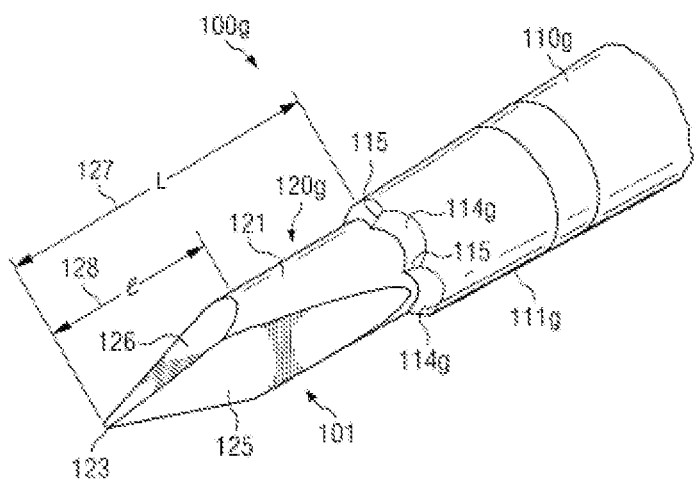
FIGS. 1C and 1D depict perspective views of a prior art IO device having a stylet disposed in the cannula of FIG. 1B.
Figure 1D:
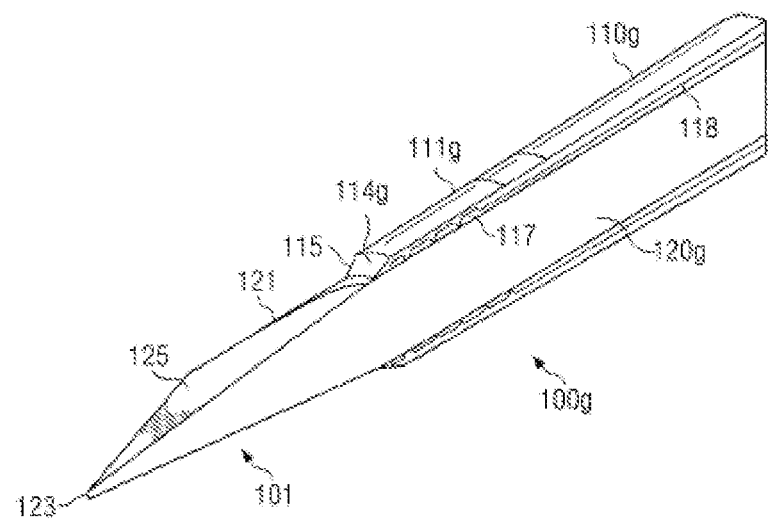

FIGS. 1B-1D show a second example of cutting surfaces and tips which may be formed adjacent to the ends of a cannula and/or an associated stylet in the present embodiments. In the embodiment shown, outer penetrator or cannula 110g may include first end 111g having a plurality of cutting surfaces 114g formed adjacent to opening 116 in first end 111g. Opening 116 may communicate with and form a portion of an associated longitudinal bore or lumen 118. For some applications cutting surfaces 114g may be formed using electrical discharge machining (EDM) techniques or otherwise, as described in WO 2008/033874. In the embodiment shown, first end 111g has a generally tapered configuration or reduced outside diameter as compared with other portions of cannula 110g In other embodiments, first end 111g has an outside diameter that is equal to the outside diameter of other portions of cannula 110g (e.g., cannula 110g can have a constant outside diameter along the entire length of the cannula). Cutting surfaces 114g may, for example, be formed using machine grinding techniques. In some embodiments, such as the one shown, end 111g of cannula 110g may include six ground cutting surfaces 114g with respective crowns 115 therebetween. Forming a biopsy needle set and/or biopsy needle with tapered end 111g and a plurality of cutting surfaces 114g and crowns 115 may provide improved drilling performance (e.g., relative to others configurations) when the resulting biopsy needle set and/or biopsy needle is used with a powered driver in accordance with teachings of the present disclosure. For some applications, a helical groove 117 may be formed within longitudinal bore 118 proximate opening 116. Helical groove 117 may assist with retaining a biopsy specimen or a bone marrow specimen within longitudinal bore 118. For example, a single thread may be disposed within the longitudinal bore or lumen of the cannula such that the helical groove 117 is defined between turns of the thread. Various techniques and procedures may be satisfactorily used to place the single thread or otherwise form the helical groove, as described WO 2008/033874.

As shown in FIG. 1C, a biopsy needle set 100g may include cannula or outer penetrator 110g with stylet or inner penetrator 120g slidably disposed therein. The proximal ends of cannula 110g and stylet 120g may be similar to those of cannula 110a and stylet 120 depicted in FIG. 1A (e.g., may include hubs 140a and 150a, respectively). For some applications first end 101 of biopsy needle set 100g may minimize damage to skin and soft body tissue at an insertion site. For some applications inner penetrator or stylet 120g may include first end 121 having a plurality of cutting surfaces 125 and 126 formed on exterior portions thereof extending from associated tip 123 towards second end of stylet or inner penetrator 120g. For some applications one or more cutting surfaces 125 may be formed having length 127 extending from tip 123 to associated cutting surfaces 114g in associated cannula 110g. One or more cutting surfaces 126 may be formed adjacent to each cutting surface 125 with second length 128. First length 127 may be greater than second length 128. As shown, lengths 127 and 128 are measured parallel to the central longitudinal axis of stylet 120g. The ratio of first length 127 and second length 128 may be varied in accordance with teachings of the present disclosure to provide optimum performance for penetrating a selected bone and associated bone marrow. Additional details of some embodiments of first end 101 are described in WO 2008/033874.

Figure 2:
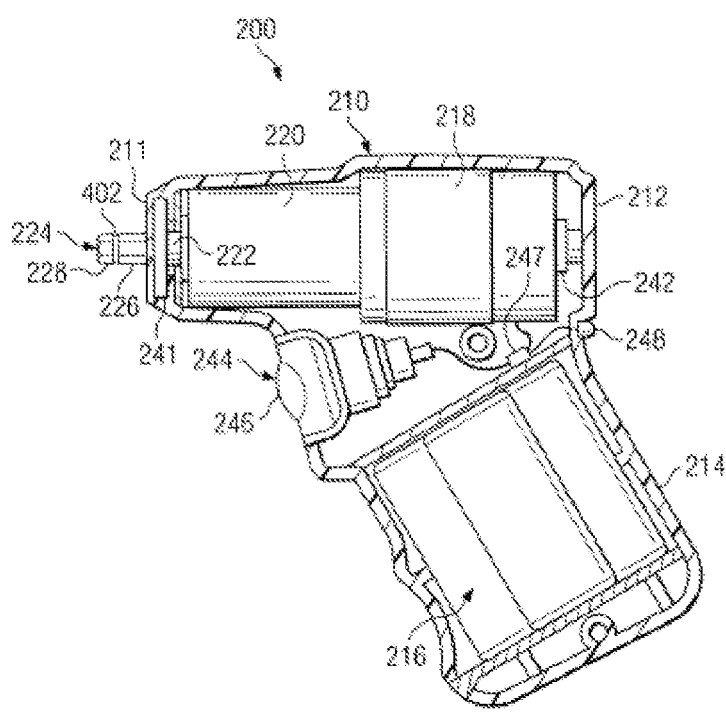
FIG. 2 depicts a cross-sectional side view of a prior art driver that may be modified to have one of the present sensors and, thus, become one of the present drivers.

FIG. 2 depicts a cross-sectional view of one embodiment of a driver that can be used with embodiments of the present drivers and kits. In the embodiment shown, powered driver 200 may be used to insert an intraosseous devices into a bone and associated bone marrow. Powered driver 200 may include housing 210 having a general configuration similar to a small pistol defined in part by handle 214. Various components associated with powered driver 200 may be disposed within housing 210 (e.g., handle 214). For example a power source such as battery pack 216 may be disposed within handle 214. Housing 210 may be formed from relatively strong, heavy duty polymeric materials such as polycarbonate or other satisfactory materials. For some applications housing 210 may be formed in two halves (not expressly shown) which may be joined together with a fluid tight seal to protect various components of powered driver 200 disposed therein.

Motor 218 and gear assembly 220 may be disposed within portions of housing 210 adjacent to handle 214. Motor 218 and gear assembly 220 may be generally aligned with each other. Motor 218 may be rotatably engaged with one end of gear assembly 220. Drive shaft 222 may be rotatably engaged with and extend from another end of gear assembly 220 opposite from motor 218. For some applications both motor 218 and gear assembly 220 may have generally cylindrical configurations. Distal end or first end 211 of housing 210 may include an opening with portions of drive shaft 222 extending through the opening, as shown. For some applications, end 224 or the portion of drive shaft 222 extending from first end 211 of housing 210 may have a generally hexagonal cross section with surfaces 226 disposed thereon. Receptacle 263 disposed in second end 252 of coupler assembly 250 may have a matching generally hexagonal cross section, as shown in FIGS. 6A-6C.

Surfaces 226 may extend generally parallel with each other and parallel with respect to a longitudinal axis or rotational axis of drive shaft 222. One or more tapered surfaces 228 may also be formed on end 224 to assist with releasably engaging powered driver 200 with coupler assembly 250. Embodiments of powered driver 200 include speed reduction ratios, for example, of between 60:1 and 80:1, resulting in drive shaft RPMs that are reduced relative to motor RPMs. Coupler assemblies having corresponding openings or receptacles may be releasably engaged with end 224 extending from first end 211 of powered driver 200. For example, end 224 extending from first end 211 of housing 210 may be releasably engaged with receptacle 264 disposed proximate second end 252 of coupler assembly 250, as shown in FIGS. 6A-6B.

For some applications thrust bearing 241 may be disposed between first end or distal end 211 of housing 210 and adjacent portions of gear assembly 220. Thrust bearing 242 may be disposed between second end or proximal end 212 of housing 210 and adjacent portions of motor 218. Thrust bearings 241 and 242 may limit longitudinal movement of motor 218, gear assembly 220 and drive shaft 222 within associated portions of housing 210. Trigger assembly 244 may also be disposed within housing 210 proximate handle 214. Trigger assembly 244 may include trigger or contact switch 246. Motor 218 may be energized and deenergized by alternately depressing and releasing trigger 246. Electrical circuit board 247 may also be disposed within housing 210. Electrical circuit board 247 may be electrically coupled with trigger assembly 244, motor 218, power supply 216 and indicator light 248. For some applications indicator light 248 may be a light emitting diode (LED) or a small more conventional light bulb. For some applications indicator light 248 may be activated when ninety percent (90%) of electrical storage capacity of battery pack 216 has been used. The configuration and dimensions of an intraosseous device formed in accordance with teachings of the present disclosure may vary depending upon respective intended applications for each intraosseous device. For example the length of a biopsy needle formed in accordance with teachings of the present disclosure may vary from approximately five (5) millimeters to thirty (30) millimeters.

Coupler assemblies incorporating teachings of the present disclosure may function as "quick release mechanisms" operable to engage and disengage an IO device from a powered driver (e.g., a driver disposed within a flexible containment bag or sterile sleeve). Such coupler assemblies may allow rotation of an IO device (e.g., biopsy needle or needle set) without damage to the flexible containment bag or sterile sleeve. One end of the coupler assembly may be operable to form a fluid seal or fluid barrier with adjacent portions of the containment bag or sterile sleeve. A coupler assembly incorporating teachings of the present disclosure may also be described as a port assembly attached to a containment bag. Such port assemblies may allow easy engagement or disengagement of a powered driver from an IO device and at the same time allow the powered driver to "power in and power out" an IO device from an insertion site.

Figure 3:
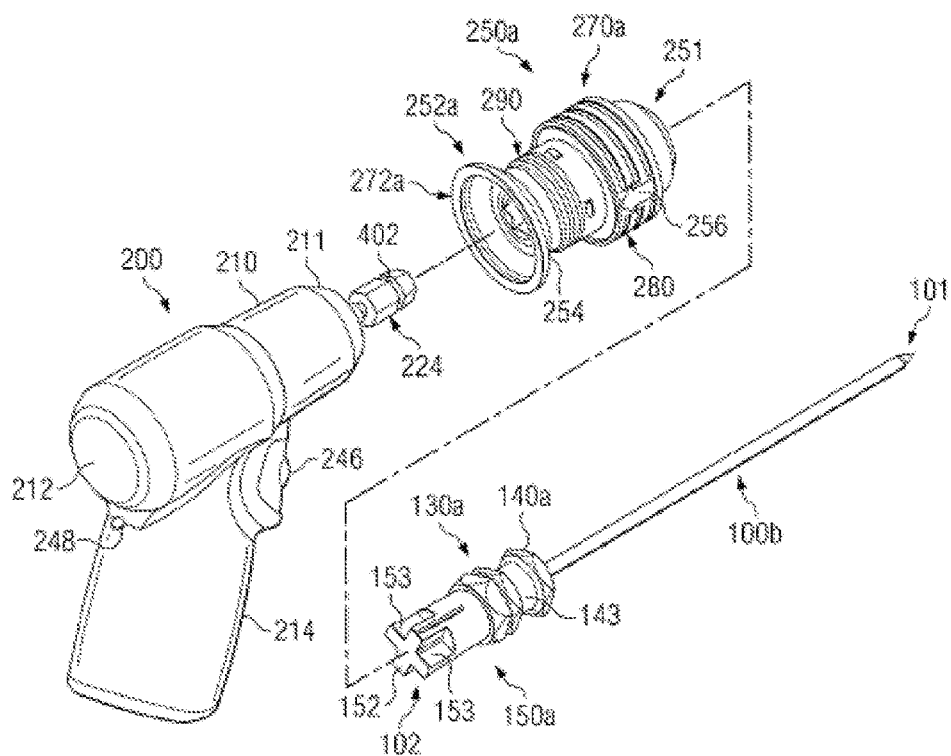
FIG. 3 depicts a perspective view of the driver of FIG. 2 with a prior art coupler assembly and a prior art JO device.
Figure 4:
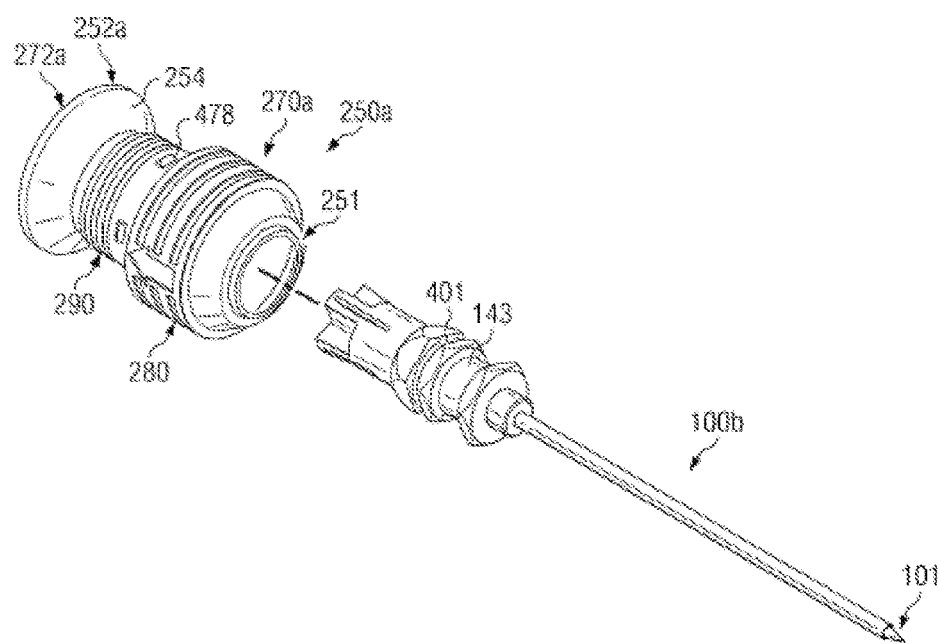
FIG. 4 depicts the coupler assembly and JO device of FIG. 3.
Figure 5:
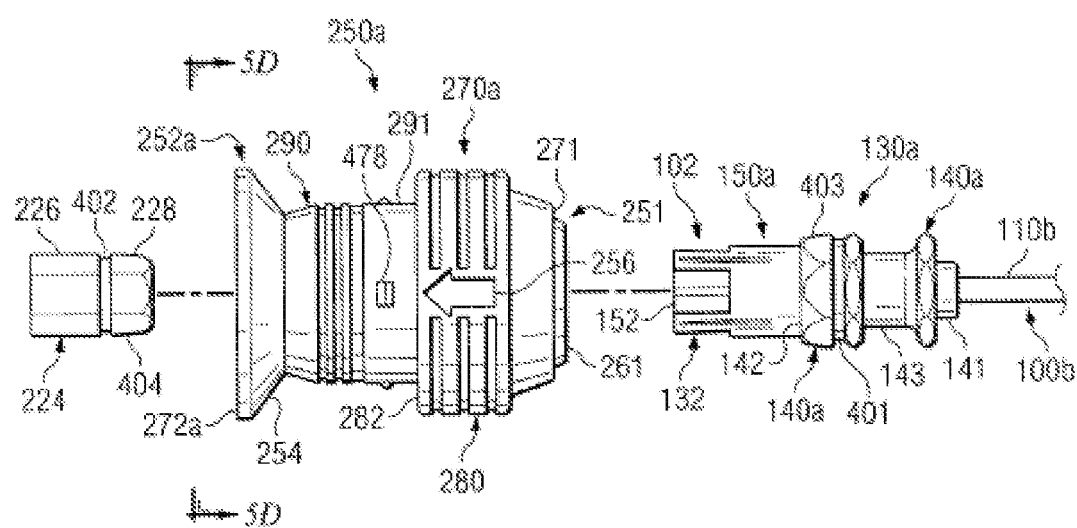
FIG. 5 depicts portions of the driver of FIG. 2 and the coupler assembly and a portion of the JO device of FIG. 3.

FIGS. 3-6C depict an example of a coupler assembly 250 suitable for some embodiments of the present assemblies and kits. FIGS. 3-5 are perspective views showing various views of powered driver 200, coupler assembly 250a, and intraosseous device 100b that is substantially similar to device 100a with the exception that device 100b does not include markings 104. Coupler assembly 250a includes a first end 251 operable to be releasably engaged with one end of an intraosseous device such as, but not limited to, second end 102 of biopsy needle set 100b. Coupler assembly 250a also includes a second end 252 operable to be releasably engaged with a portion of a drive shaft extending from a powered driver, such as, but not limited to, end 224 of drive shaft 222 extending from first end 211 of housing 210 of powered driver 200. Though not depicted here, second end 252 of coupler assembly 250 may be securely engaged with an opening in a containment bag or sterile sleeve, as described in WO 2008/033874.

Coupler assemblies incorporating various teachings of the present disclosure may be placed in a medical procedure tray or kit with one end down and an opposite end looking up to allow "hands free" releasable engagement with a powered driver or a manual driver. For example, coupler assembly 250a may be disposed in medical procedure tray with first end 251 facing downward and second end 252 facing up such that end 224 of drive shaft 222 (of driver 200) may be inserted into and releasably engaged with second end 252 of coupler assembly 250 without requiring an operator or user to physically contact or manipulate any portion of coupler assembly 250a. As described below, coupler 250a may include a "hands free" latching mechanism.

In the embodiment shown, coupler assembly 250a may include elongated core 260 with housing assembly 270 slidably disposed on exterior portions of elongated core 260. Housing assembly 270/270a may include first end 271 and second end 272 which may be generally aligned with respective first end 261 and respective second end 262 of elongated core 260. For some applications, elongated core 260 may have a generally cylindrical configuration defined in first exterior portion 260a and second exterior portion 260b with various shoulders and/or recesses formed thereon. For some embodiments first exterior portion 260a may have a larger diameter than second exterior portion 260b. Housing assembly 270 may be described as having a generally hollow, cylindrical configuration defined in part by first housing segment 280 and second housing segment 290. The first end of housing segment 280 may generally correspond with first end 271 of housing assembly 270. The second end of second housing segment 290 may generally correspond with second end 272 of housing assembly 270. First end 291 of second housing segment 290 may be described as having a generally cylindrical configuration with an outside diameter smaller than the adjacent inside diameter of second end 282 of first housing segment 280. Second housing segment 290 may slide longitudinally from a first position (FIG. 6A) to a second position (FIG. 6B) within second end 282 of first housing segment 280 to release one end of a drive shaft engaged with second end 252 of coupler assembly 250.

A biasing mechanism such as coiled spring 274 may be disposed around exterior portion 260a of generally elongated core 260. First end 275 of coiled spring 274 may contact annular shoulder 284 formed on interior portions of first housing segment 280. Second end 276 of coiled spring 274 may contact annular shoulder 278 disposed proximate first end 291 of second housing segment 290. Coil spring 274, annular shoulder 284 and annular shoulder 278 may cooperate with each other to generally maintain first housing segment 280 and second housing segment 290 in a first extended position relative to each other. Other biasing mechanisms such as, but not limited to, leaf springs and bellows (not expressly shown) may also be disposed between annular shoulder 284 and annular shoulder 278. Annular shoulder 278, associated with second end 276 of coiled spring 274, may extend radially outward from generally cylindrical ring 277. Generally cylindrical ring 277 may be slidably and rotatably disposed on exterior portion 260a of elongated core 260. Annular shoulder 279 may be disposed on interior portions of generally cylindrical ring 277 and may extend radially inward toward adjacent portions of elongated core 260. Annular shoulder 268 may be formed on exterior portion 260a of elongated core 260 intermediate first end 261 and second end 262. The configuration and dimensions of annular shoulder 268 and annular shoulder 279 are selected to be compatible with each other such that engagement between annular shoulder 279 of generally cylindrical ring 277 with annular shoulder 268 of elongated core 260 may limit movement of second housing segment 290 longitudinally in the direction of second end 262 of elongated core 260.

For some applications a plurality of flexible collets or fingers 477 may extend from generally cylindrical ring 277 opposite from annular shoulder 278. Respective collet heads 478 may be formed on the end of each collet 477 opposite from annular shoulder 278. The dimensions and configuration of collet heads 478 may be selected to be received within respective slots or openings 297 formed in second housing 290. During manufacture of coupler assembly 250a, each collet head 478 may be disposed within respective slot or opening 297 to securely engage generally cylindrical ring 277 and annular shoulder 278 proximate first end 291 of second housing segment 290. As a result, second housing segment 290 and annular shoulder 278 may generally move as a single unit relative to elongated core 260 and first housing segment 280. During disengagement of an intraosseous device from first end 251 of coupler assembly 250a, first housing segment 280 may move or slide longitudinally toward second housing segment 290. In a similar manner, second housing segment 290 may move or slide longitudinally toward first housing segment 280 during disengagement of a powered driver from second end 252 of coupler assembly 250a.

Annular shoulder 267 may be formed on exterior portions of elongated core 260 proximate first end 261. Annular shoulder 267 may engage portions of first end 271 of housing 270 to limit longitudinal movement of first housing segment 280 during longitudinal movement of second housing segment 290 towards first end 261 of elongated core 260 during disengagement of a powered driver from second end 252 of coupler assembly 250a. As previously noted, annular shoulder 268 may be formed on exterior portions of elongated core 260 between first end 261 and second end 262. Engagement between annular shoulder 268 and annular shoulder 279 of generally cylindrical ring 277 may limit movement of second housing segment 290 toward second end 262 of elongated core 260. Contact between spring 274 and annular shoulder 278 and annular shoulder 284 of first housing segment 280 may limit the longitudinal movement of first housing segment 280 in the direction of second end 262 of elongated core 260 during disengagement of an intraosseous device from first end 251 of coupler assembly 250a.

Generally cylindrical ring 277 and attached annular shoulder 279 may slide longitudinally on exterior portions of annular core 260 between annual shoulder 268 and annular shoulder 267. First housing segment 280 may move longitudinally toward second end 262 of elongated core 260 to release one end of intraosseous device from engagement with first end 251 of coupler assembly 250a. In a similar manner, second housing segment 290 may move longitudinally toward first end 261 of elongated core 260 to release one end of a drive shaft extending from a powered driver engaged with second end 252 of coupler assembly 250a. A wide variety of latches and latch mechanisms may be satisfactorily used to releasably engage one end of an intraosseous device within a first end of a coupler assembly incorporating teachings of the present disclosure. In a similar manner, a wide variety of latches and latch mechanisms may be satisfactorily used to releasably engage one end of a drive shaft extending from a powered driver or manual driver within a second end of the coupler assembly incorporating teachings of the present disclosure.

For embodiments represented by coupler assembly 250a, first latch 410 may be disposed on exterior portions of elongated core 260 proximate receptacle 263 adjacent to first end 261 to releasably engage one end of an IO device such as second end 102 of biopsy needle set 100b within receptacle 263 of coupler assembly 250a. Second latch mechanism 420 may be disposed on exterior portions of elongated core 260 proximate receptacle 264 adjacent to second end 262 to releasably engage one end of a drive shaft with second end 252 of coupler assembly 250a. Second latch 420 may be used to releasably engage one portion of a drive shaft such as end 224 of drive shaft 222 extending from powered driver 200 within second end 252 of coupler assembly 250a. Latch 410 may releasably engage an intraosseous device with first end 251 of coupler assembly 250a and substantially the same latch 420 may releasably engage a powered driver with second end 252 of coupler assembly 250a.

For some applications, latches 410 and 420 may have similar configurations such as a general "omega" shape (e.g., latch 420). However, latch 410 may have larger dimensions corresponding generally with exterior portion 260a of elongated core 260. Latch 420 may have smaller dimensions corresponding generally with exterior portion 260b of elongated core 260. Various features of the present disclosure may be described with respect to latch mechanism 420 along with adjacent portions of second housing segment 290 and exterior portion 260b of elongated core 260. Respective detents 421 and 422 may be formed on opposite ends of generally omega shaped latch 420. In a similar manner, respective detents (not expressly shown) may be formed on the ends of generally omega shaped latch 410. The configuration and dimensions of detents 421 and 422 may be compatible with placing each detent 421 and 422 in a respective slot or opening extending between exterior portion 260b of elongated core 260 to interior portions of receptacle 264 disposed proximate second end 252 of coupler assembly 250a. Latch 420 may have a first position in which portions of detents 421 and 422 may extend through the respective slots. The dimensions and configuration of detent 421 and 422 may be operable to be securely engaged with annular groove 402 formed in end 224 of powered driver 200. In a similar manner, respective detents on associated latch 410 may be releasably engaged with annular groove 401 disposed in second end 102 of biopsy needle 100b. For some applications, a plurality of tapered surfaces 403 may be formed on exterior portions of hub 140a proximate first end 142 to radially expand detent mechanisms associated with omega shaped latch 410 radially outward while inserting second end 102 of biopsy needle 100b into first end 251 of coupler assembly 250a. The detent mechanism may "snap" into annular groove 401 when aligned therewith. In a similar manner, a plurality of tapered surfaces 228 may be formed on exterior portions of end 224 of drive shaft 222 extending from powered driver 200 to radially expand detent mechanisms 421 and 422 radially outward during the insertion of end 224 of powered driver 200 into second end 252 of coupler assembly 250a. Detent mechanisms 421 and 422 will "snap" into annular groove 402 when aligned therewith.

Engagement between detent mechanisms associated with latch 410 with annular groove 401 of hub assembly 130a will generally retain second end 102 of biopsy needle 100b securely engaged with first end 251 of coupler assembly 250a. This engagement may allow powered driver 200 to rotate or spin cannula or biopsy needle 110b while withdrawing cannula or biopsy needle 110b from an insertion site. In a similar manner, engagement between detent mechanisms 421 and 422 of omega shaped latch 420 and annular groove 402 of end 224 of powered driver 200 will generally retain second end 252 of coupler assembly 250a engaged with powered driver 100 during withdrawal of cannula 110b from an insertion site.

Biopsy needle set 100b may be released from first end 251 of coupler assembly 250a by sliding first housing segment 280 longitudinally toward second end 262 of elongated core 260. Such movement of first housing segment 280 will result in interior tapered surface 286 contacting exterior portions of omega shaped latch 410 and compressing omega shaped latch 410 to radially expand associated detent mechanisms (not expressly shown) from engagement with annular groove 401 of hub assembly 130a. As a result, biopsy needle set 100b may be easily withdrawn from first end 251 of coupler assembly 250a. In a similar manner, longitudinal movement of second housing segment 290 toward first end 251 of coupler assembly 250a will result in interior tapered surface 296 contacting exterior portions of omega shaped latch 420 to compress generally omega shaped latch 420 and withdraw or retract detent mechanisms 421 and 422 from engagement with annular groove 402 of end 224. As a result, powered driver 200 and second end 222 of coupler assembly 250a may be easily disconnected from each other.

Flange 254 may be generally described as having an enlarged funnel shaped or bell shaped configuration. The dimensions and configuration of flange 254 may be selected to be compatible with end 211 of powered driver 200. As previously noted, coupler assembly 250a may be securely engaged with an opening formed in a containment bag or sterile sleeve in accordance with teachings of the present disclosure. For embodiments such as the one shown, end 272 of housing 270 of coupler assembly 250a may include annular ring 370 operable to be securely engaged with adjacent portions of flange 254. The outside diameter of annular ring 370 may generally correspond with the outside diameter of adjacent portions of flange 254. The inside diameter of annular ring 370 may also generally correspond with the inside diameter of adjacent portions of flange 254. For some embodiments a plurality of posts 372 and generally V shaped grooves 374 may be alternatingly disposed on the extreme end of flange 254. Annular ring 370 may include a plurality of holes 371 sized to received respective posts 372 therein. Annular ring 370 may also include a plurality of generally V shaped projections 376 sized to be received within respective generally V shaped grooves 374 formed in adjacent portions of flange 254. For embodiments such as the one shown, portions of a containment bag (e.g., around an opening) may be disposed between annular ring 370 and adjacent portions of flange 254. For example, post 372 may be inserted through a corresponding hole in a containment bag adjacent to the perimeter of an opening in the containment bag. Holes 371 in annular ring 370 may be aligned with respective posts 372. Other portions of a containment bag (e.g., adjacent to an opening) may be trapped between respective V shaped projections 376 and V shaped grooves 374. Various welding techniques including, but not limited to, laser welding may be applied to posts 372 to bond annular ring 370 with adjacent portions of flange 354. As a result, a perimeter of a containment bag around an opening in the containment bag may be securely engaged with second end 252 of coupler assembly 250a.

Figure 7A:
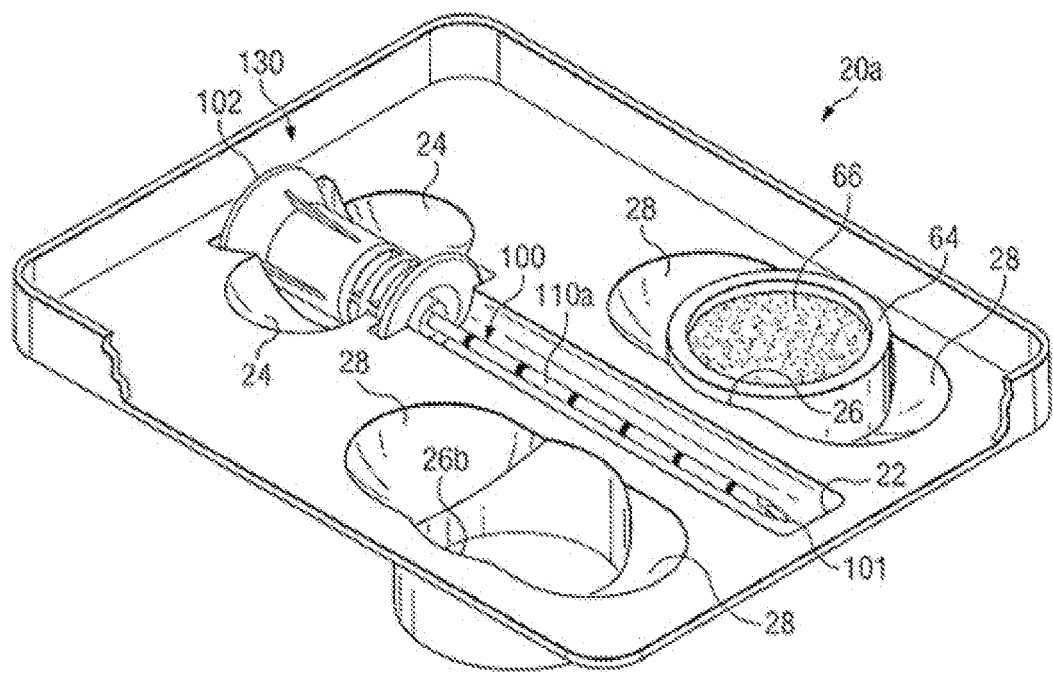
FIGS. 7A-7C depict various views of prior art kits.
Figure 7B:
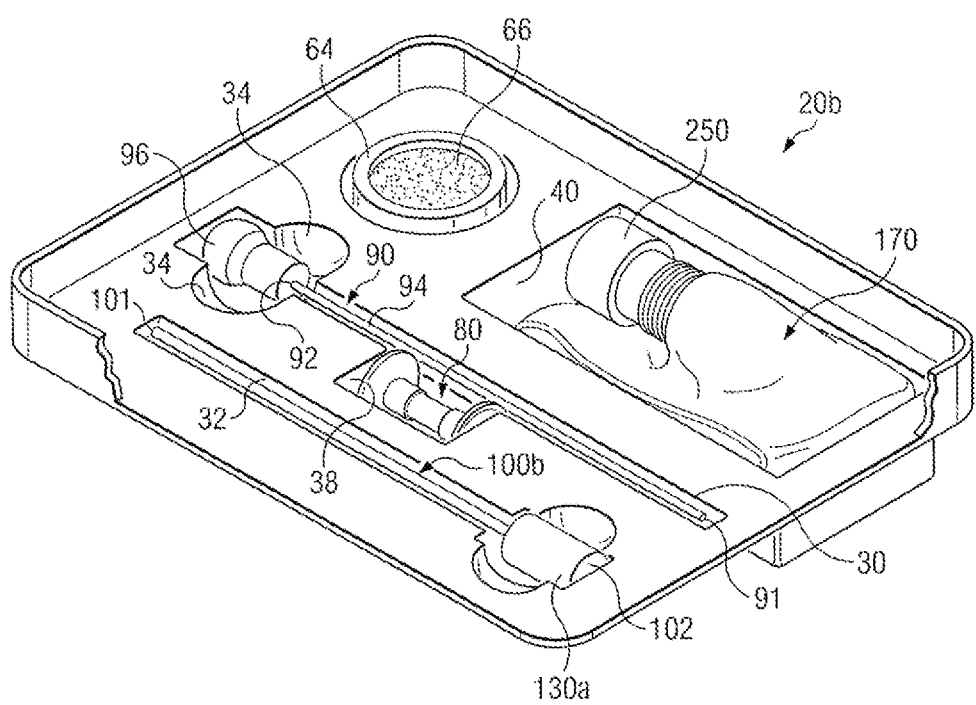
Figure 7C:
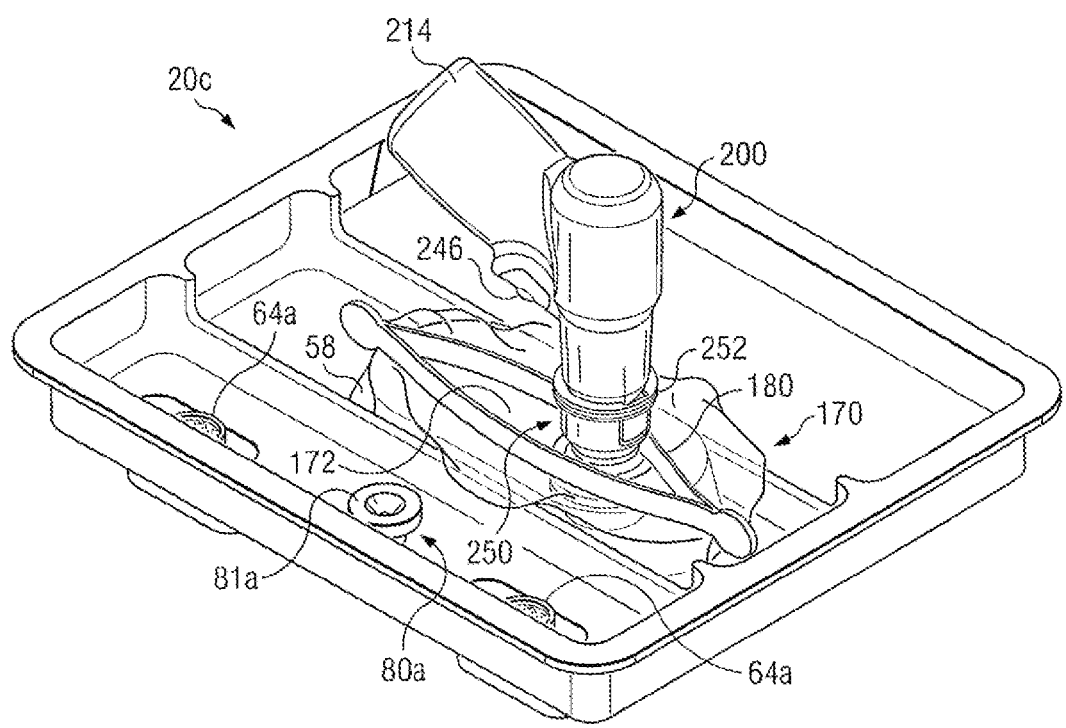

FIGS. 7A-7C show some examples of medical procedure trays and/or kits which may contain one or more intraosseous devices and/or other components incorporating teachings of the present disclosure. For example, medical procedure tray 20a as shown in FIG. 7A may include intraosseous needle set or aspiration needle set 100 incorporating various teachings of the present disclosure. Medical procedure tray 20b as shown in FIG. 7B may include intraosseous needle set or biopsy needle set 100b, ejector 90, funnel 80 and/or containment bag or sterile sleeve 170. Medical procedure tray 20c as shown in FIG. 7C may also include various IO devices and other components incorporating teachings of the present disclosure including, but not limited to, biopsy needle set 100b, coupler assembly 250, containment bag 170, ejector 90 and/or funnel 80a.

Medical procedure trays and/or kits formed in accordance with teachings of the present disclosure may provide a support or base for various components such as a coupler assembly, funnel, and/or sharps protector to allow an operator or user to perform various functions without requiring that the operator or user hold or manipulate the respective component. For example, medical procedure tray 20c as shown in FIG. 7C may position and support coupler assembly 250 such that one end of a powered driver may be inserted (pushed) into releasable engagement with second end 252 of coupler assembly 250. The powered driver may then be used to withdraw coupler assembly 250 from medical procedure tray 20c without requiring an operator or user to directly hold or manipulate coupler assembly 250.

Medical procedure trays 20a, 20b and/or 20c may also contain a wide variety of other components including, but not limited to, one or more sharps protectors 64 as shown in FIGS. 7A and 7B. Sharps protectors 64 may include hard foam or claylike material 66 disposed therein. Intraosseous devices such as aspiration needle sets and biopsy needle sets typically have respective sharp tips and/or cutting surfaces operable to penetrate skin, soft tissue and bone. The sharp tips and/or cutting surfaces of such intraosseous devices may be inserted into hard foam or claylike material 66 after completion of a medical procedure using the respective intraosseous device.

FIG. 7C shows one procedure for placing a powered driver within a containment bag incorporating teachings of the present disclosure. Containment bag 170 may be formed from generally flexible, fluid impervious material which may also be sterilized using conventional sterilization techniques. Containment bag 170 may be used to prevent a non-sterile powered driver from contaminating a sterile intraosseous device and/or an injection site, particularly during a bone marrow biopsy procedure or a bone marrow aspiration procedure. Containment bag 170 may be operable to form a fluid barrier with adjacent portions of housing assembly 270. At the same time, coupler assembly 250 may allow powered driver to rotate an intraosseous device releasably engaged with first end 251 of coupler assembly 250 without damage to containment bag 170.

Figure 10A:
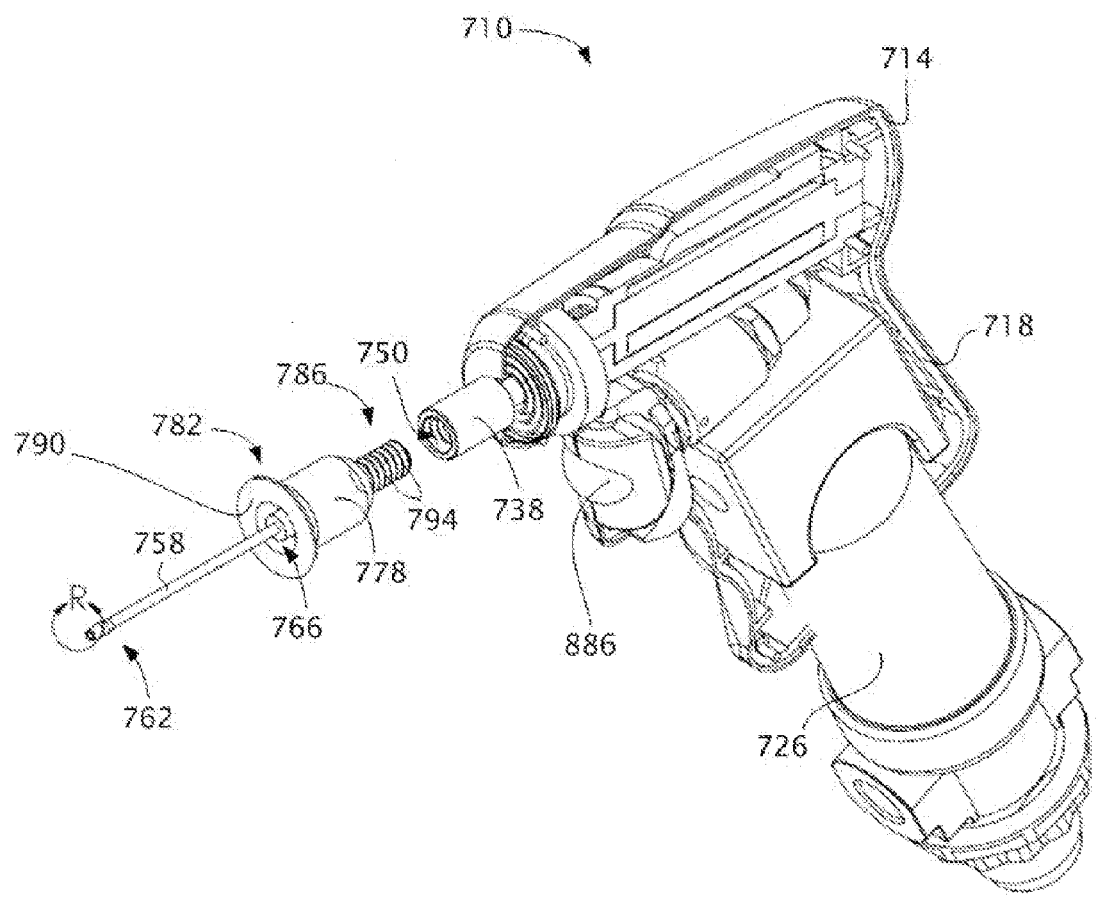
FIG. 10A depicts a cutaway perspective view of one embodiment of the present pneumatic drivers.
Figure 10B:
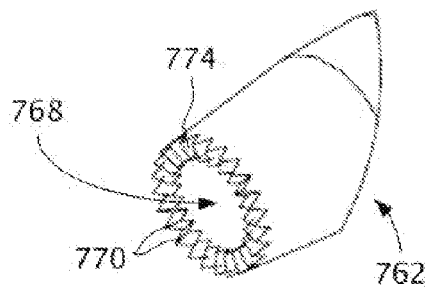
FIG. 10B depicts the distal cutting end of one embodiment of an intraosseous device that can be coupled to the driver of FIG. 10A.
Figure 10C:
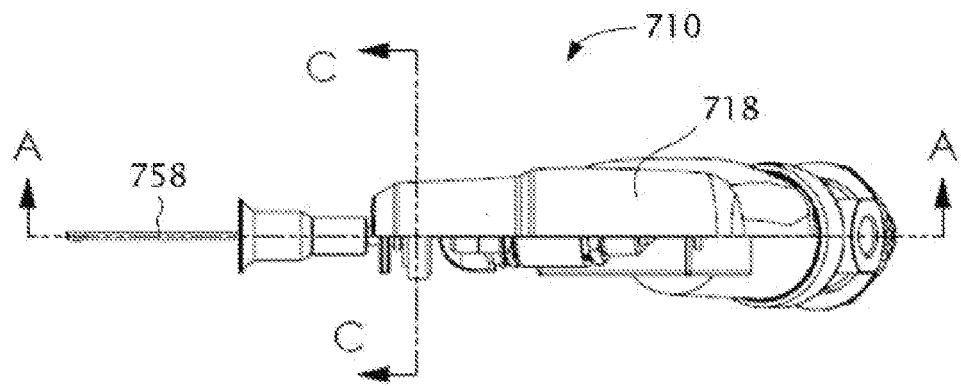
FIG. 10C depicts a top cutaway view of the driver of FIG. 10A.
Figure 10D:
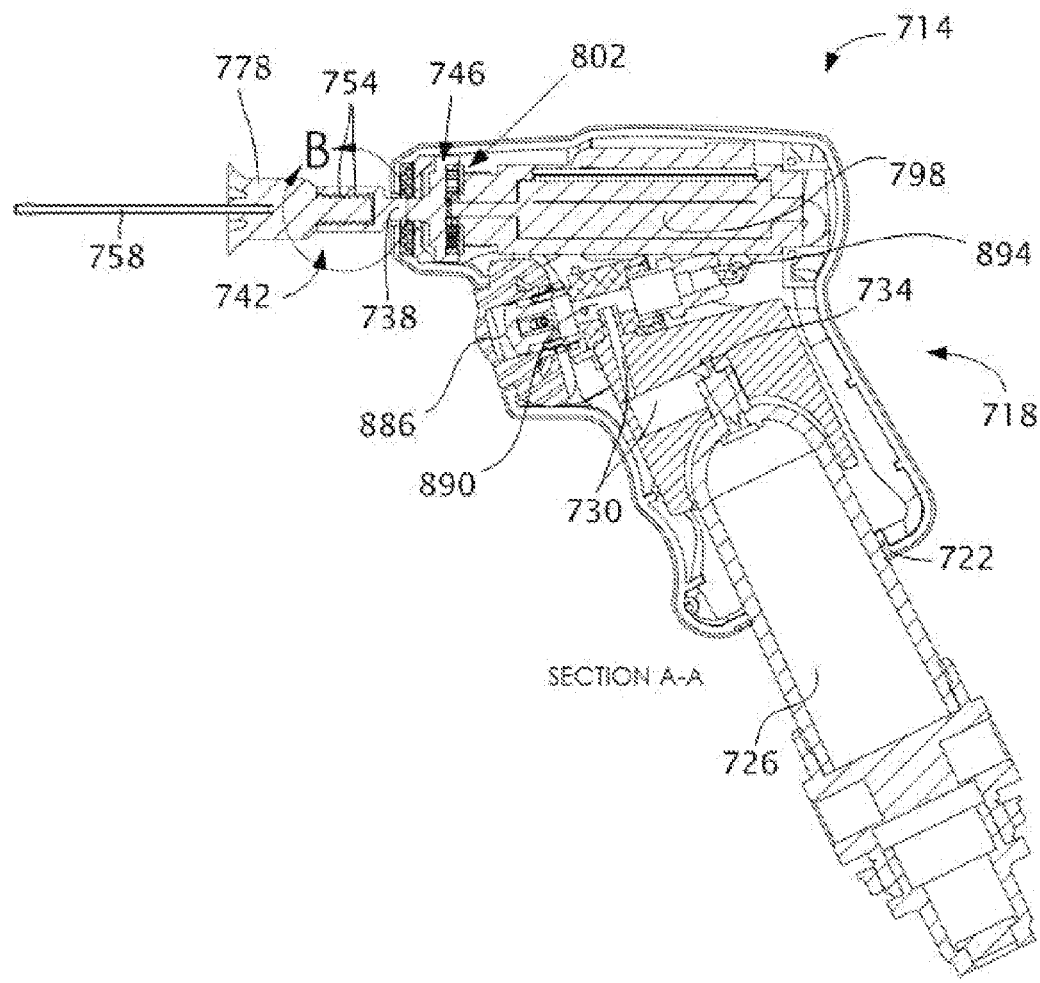
FIG. 10D depicts a side cross-sectional view of the driver of FIG. 10A.
Figure 10E:
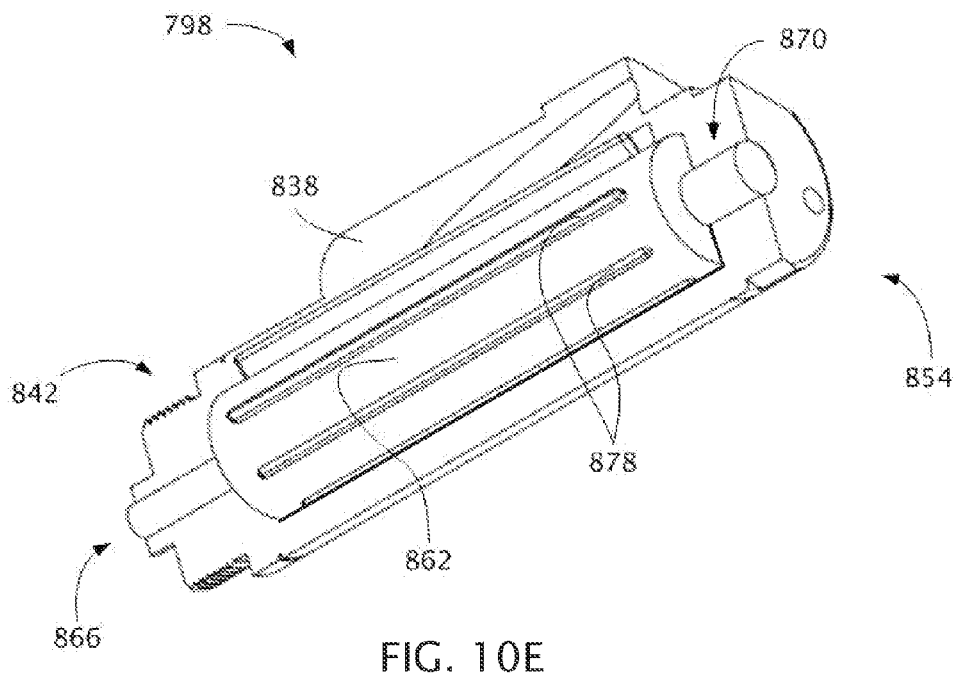
FIGS. 10E-10F depict cutaway perspective and side views, respectively, of one embodiment of the motor assembly of the driver of FIG. 10A.
Figure 10F:
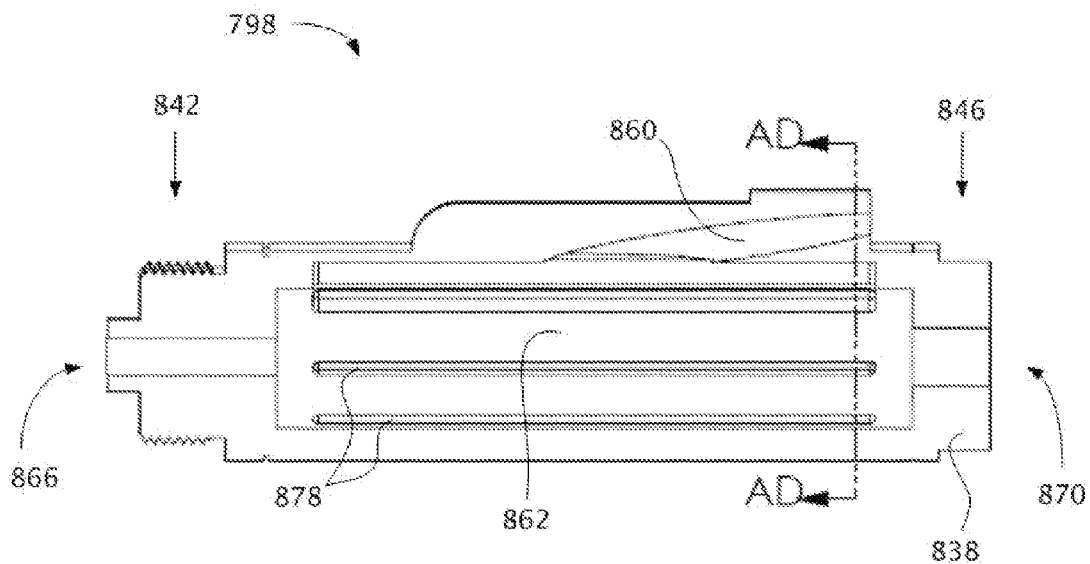
Figure 10G:
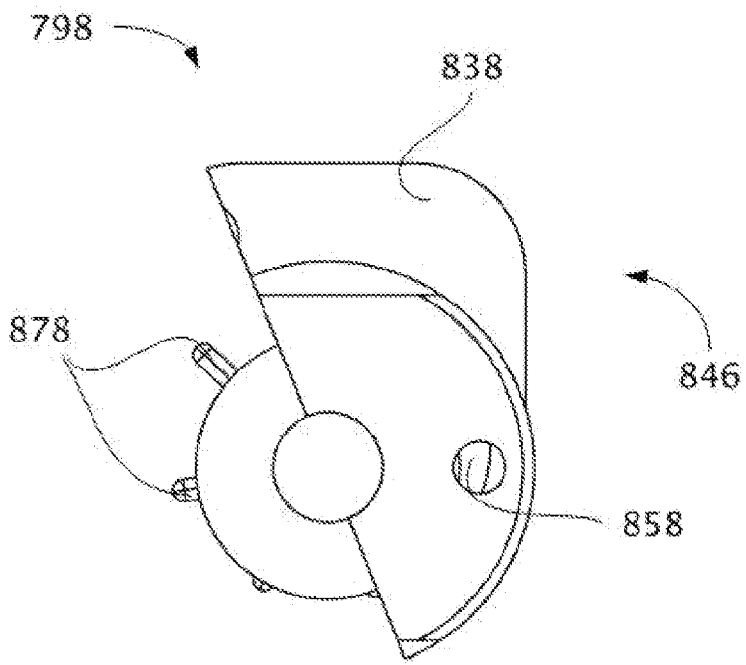
FIGS. 10G-10H depict cutaway end and cross-sectional views, respectively, of the motor assembly of FIGS. 10E-10F.
Figure 10H:
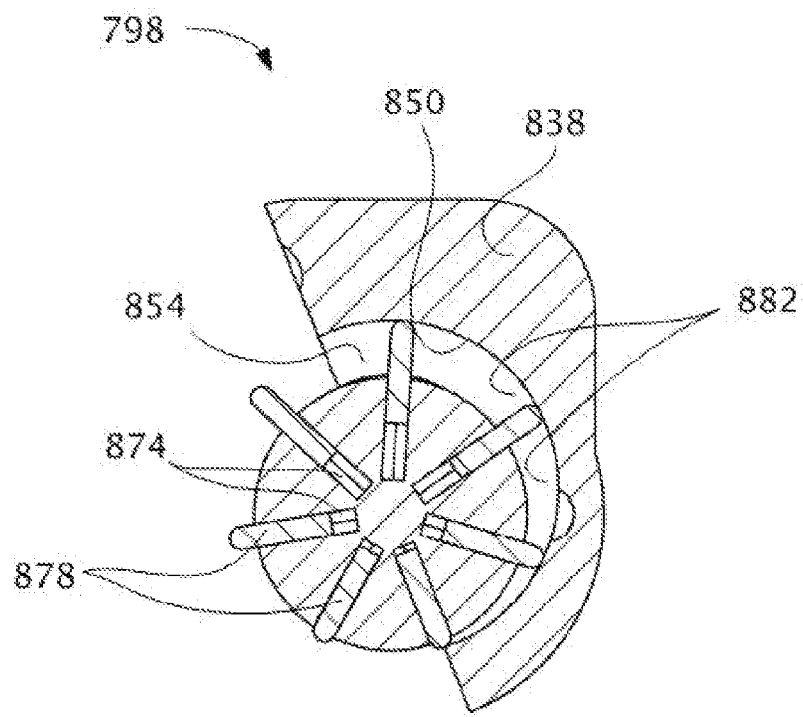

FIGS. 8A-8G depict an embodiment 510 of the present drivers. As with the drivers previously described in this disclosure, driver 510 can be manual or powered and can be configured, for example, to rotate and/or move intraosseous devices to penetrate a target area. Embodiments of driver 510 can comprise—but are not required to comprise—one or more components and/or characteristics of any of the other drivers described and depicted throughout this disclosure (e.g., FIG. 2, FIG. 10A, etc.). In the embodiment shown, driver 510 comprises housing 514, which has a configuration similar to a pistol (e.g., having a barrel-shape and a handle). Various components (e.g., a motor, a power source, and the like) associated with driver 510 can be disposed, at least partially, within housing 514. Housing 514 can comprise substantially rigid polymeric material (e.g., a polycarbonate) and, in some embodiments, housing 514 can comprise a single piece of material; in other embodiments, housing 514 can comprise more than one piece of material (e.g., two halves coupled with a fluid tight seal). In the embodiment shown, housing 514 includes handle 518, which can have various configurations, including, for example, being configured to be gripped by a user.

In the embodiment shown, driver 510 comprises drive shaft 522. Drive shaft 522 can be configured similarly to other embodiments of drive shafts described and depicted throughout this disclosure (e.g., FIG. 2). For example, in some embodiments, drive shaft 522 can have a substantially hexagonal cross-section (e.g., corresponding to a coupler assembly (e.g., the coupler assembly depicted in FIG. 6C)). In other embodiments, drive shaft 522 can have a cross-section with any shape configured to be coupled to a corresponding intraosseous device, such as a drill bit, a needle set, a coupler assembly, a hub, and/or the like.

In the embodiment shown, driver 510 can further comprise bearing 524 coupled to housing 514. Drive shaft 522 is configured to extend through bearing 524 such that driver 522 can move (e.g., rotate) without directly contacting housing 524.

In the embodiment shown, drive shaft 522 can be configured to be coupled (e.g., directly or indirectly) to any of the intraosseous devices (e.g., cannulas, stylets, and drill bits) and/or any of the coupling devices (e.g., coupler assemblies and hubs) described in this disclosure. For example, drive shaft 522 can be configured to be coupled to a cannula configured to penetrate a target area (e.g., skin, soft tissue, bone, and/or the like). A cannula can have a first end, a second end, and a bore extending between the first end and the second end (e.g., a portion of which is depicted in FIG. 1B). The first end of the cannula can comprise at least one cutting surface and/or a plurality of crowns having at least one cutting surface between adjacent crowns (e.g., similarly to the embodiments shown in FIGS. 1B-1D). Drive shaft 522 can be coupled to a cannula by a first hub (e.g., first hub 140a, as depicted in FIG. 1A). A first hub can be coupled (e.g., securely or removably) to a shaft of a cannula (e.g., proximate the cannula's second end). A first hub can comprise any coupling configuration operable to couple (e.g., directly or indirectly) a cannula to drive shaft 522 (e.g., such as a Luer lock fitting configured to be coupled to second hub 150a in FIG. 1A). Further, in some embodiments, a first hub can be configured to limit the depth to which a cannula can penetrate a target area (such as, for example, through a depth limiter (e.g., similarly to first hub 140a in FIG. 1A)). In the embodiment shown, a first hub can be configured to be coupled to a variety of structures, including, for example, a fluid bag (e.g., an IV fluid bag) and an aspiration device (e.g., a device configured to aspirate a target area). A configuration of a first hub can vary depending on the device to which the first hub will be coupled, if any.

As another example, driver 510, and more particularly drive shaft 522, can be coupled (e.g., directly or indirectly) to a stylet (or trocar) configured to be disposed in a bore of a cannula (e.g., as depicted in FIG. 1A). In some embodiments, a stylet can cooperate with a first end of a cannula to define a tip (e.g., a substantially planar tip) for penetrating a target area (e.g., as shown in the embodiment depicted in FIG. 1C). In some embodiments (e.g., as depicted in FIG. 1C), a first end of a stylet can have at least one tip, at least one first tapered cutting surface extending a first length from the tip, and at least one second tapered cutting surface extending a second length from the tip (e.g., in some embodiments, the first length of the first tapered cutting surface can be less than the second length of the second tapered cutting surface, but is not required to be). In still other embodiments, a first end of a stylet can comprise a surface (e.g., a blunted surface) configured to evacuate a sample from a target area (e.g., located in biological material, such as tissue, bone, bone marrow, etc.) from a bore of a cannula. Such a stylet can include a second hub (e.g., hub 150a in FIG. 1A), which can be configured to be coupled to drive shaft 522, coupler assemblies (e.g., as depicted in FIG. 4), and/or a first hub of a cannula (e.g., by threads, a Luer lock fitting, and/or the like, permitting the stylet and cannula to rotate in fixed relation to one another, as depicted in FIG. 1A).

In some embodiments, a coupler assembly (e.g., coupler assembly 250a as depicted in FIG. 3) can couple (e.g., directly or indirectly) drive shaft 522 to intraosseous devices (e.g., a cannula, a stylet, etc.), a first hub, and/or a second hub. Examples of coupler assemblies are depicted in FIGS. 3-6C.

In the embodiment shown, driver 510 comprises motor 526. Motor 526 can be—but is not required to be—configured similarly to and/or comprise similar characteristics as motor 218 depicted in FIG. 2. In the embodiment shown, motor 526 comprises motor shaft 530. Motor 526 can be coupled to a power source (e.g., one or more batteries as depicted in FIG. 2). Further, motor 526 can be coupled to trigger 534, which can be—but is not required to be—configured similarly to and/or comprise similar characteristics as trigger assembly 244 depicted in FIG. 2. In the embodiment shown, trigger 534 is configured to activate motor 526 to move drive shaft 522 (e.g., by completing an electrical circuit to power motor 526).

Figure 8A:
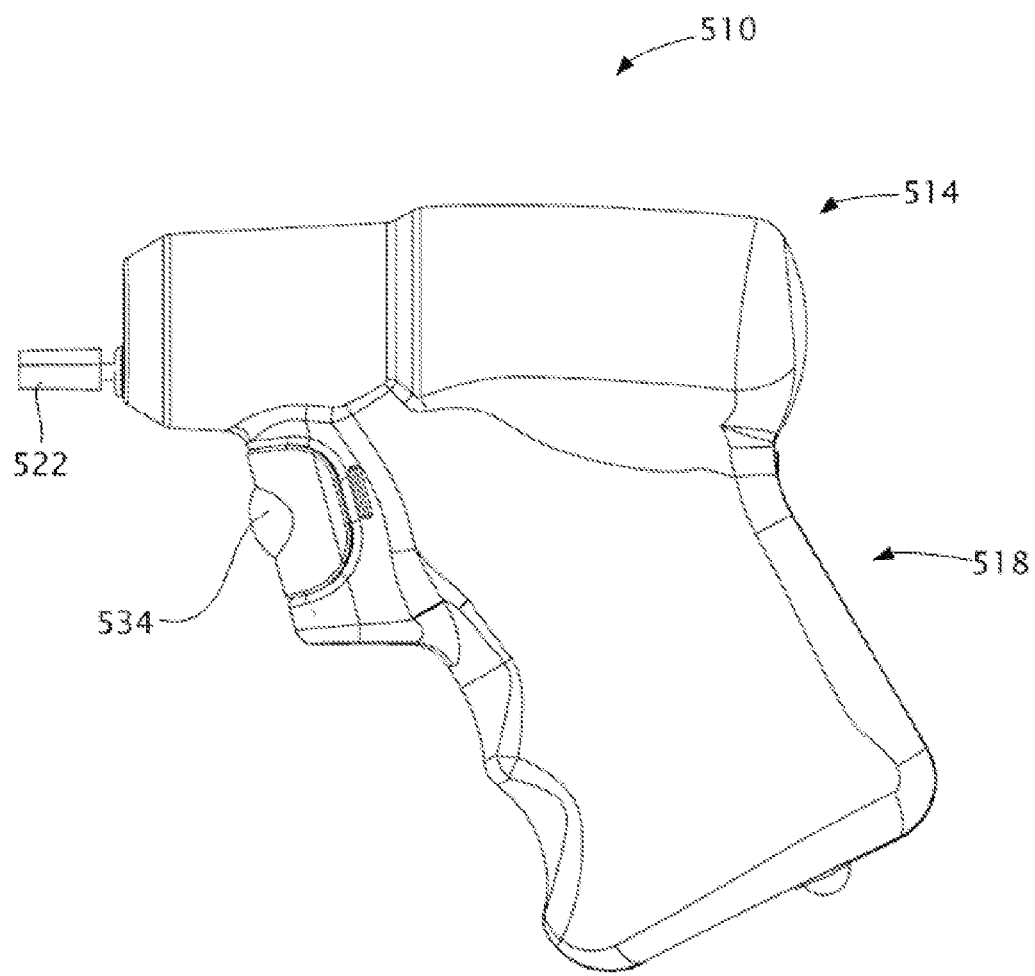
FIG. 8A depicts a side view of an embodiment of the present drivers comprising a non-geared off-axis drive system.
Figure 8B:
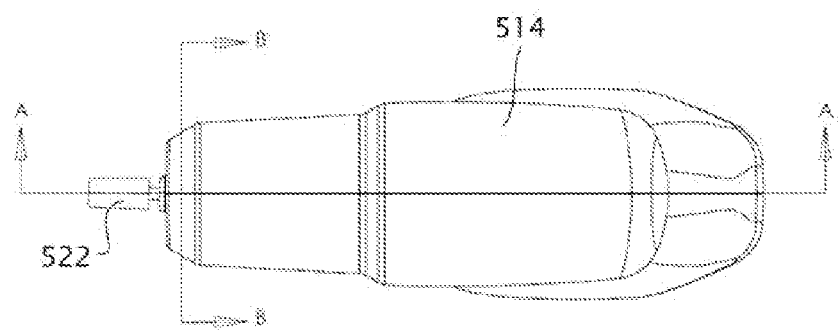
FIG. 8B depicts a top view of the driver of FIG. 8A.
Figure 8C:
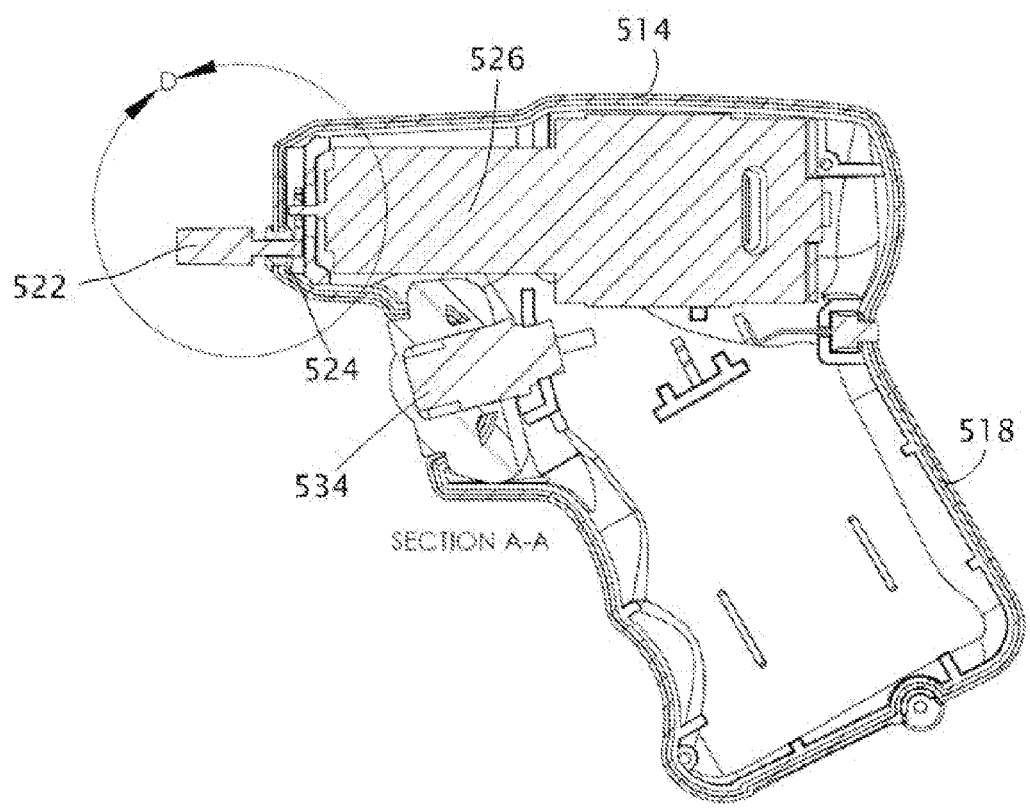
FIG. 8C depicts a cross-sectional view of the driver of FIG. 8A taken along the line A-A of FIG. 8B.
Figure 8D:
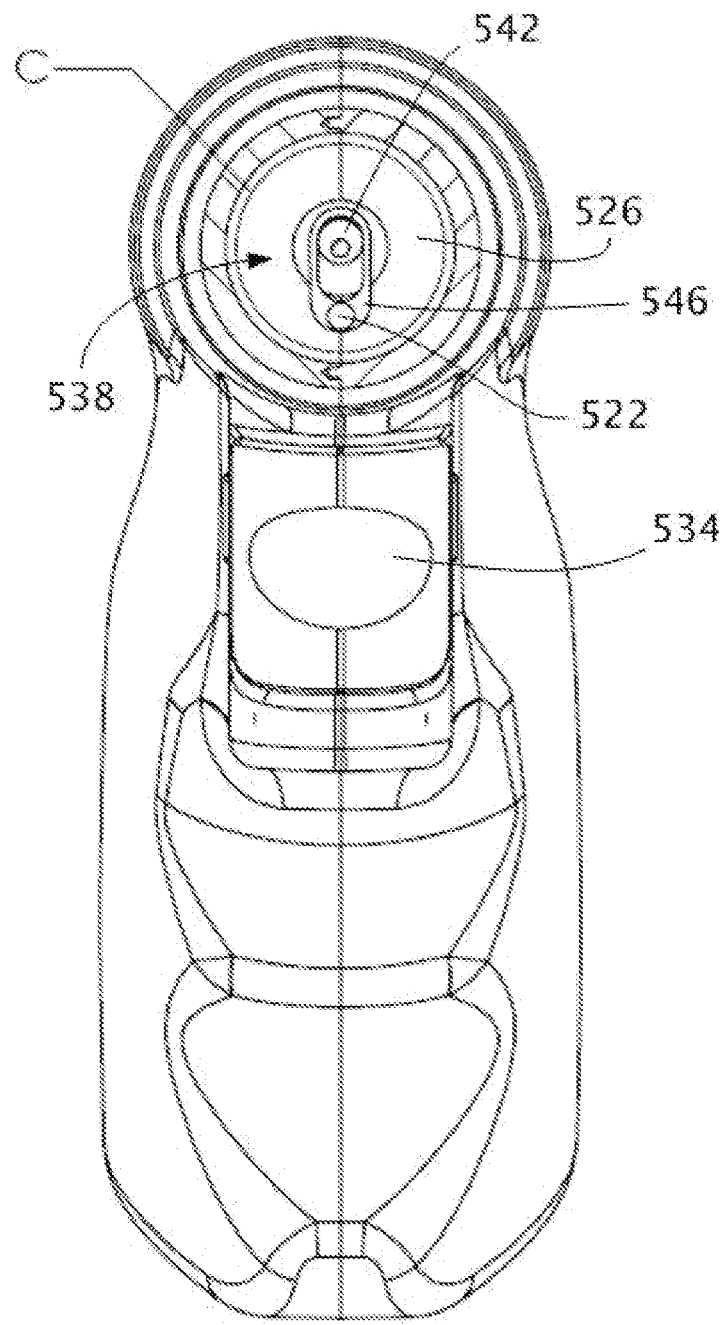
FIG. 8D depicts a cross-sectional view of the driver of FIG. 8A taken along the line B-B of FIG. 8B.
Figure 8E:
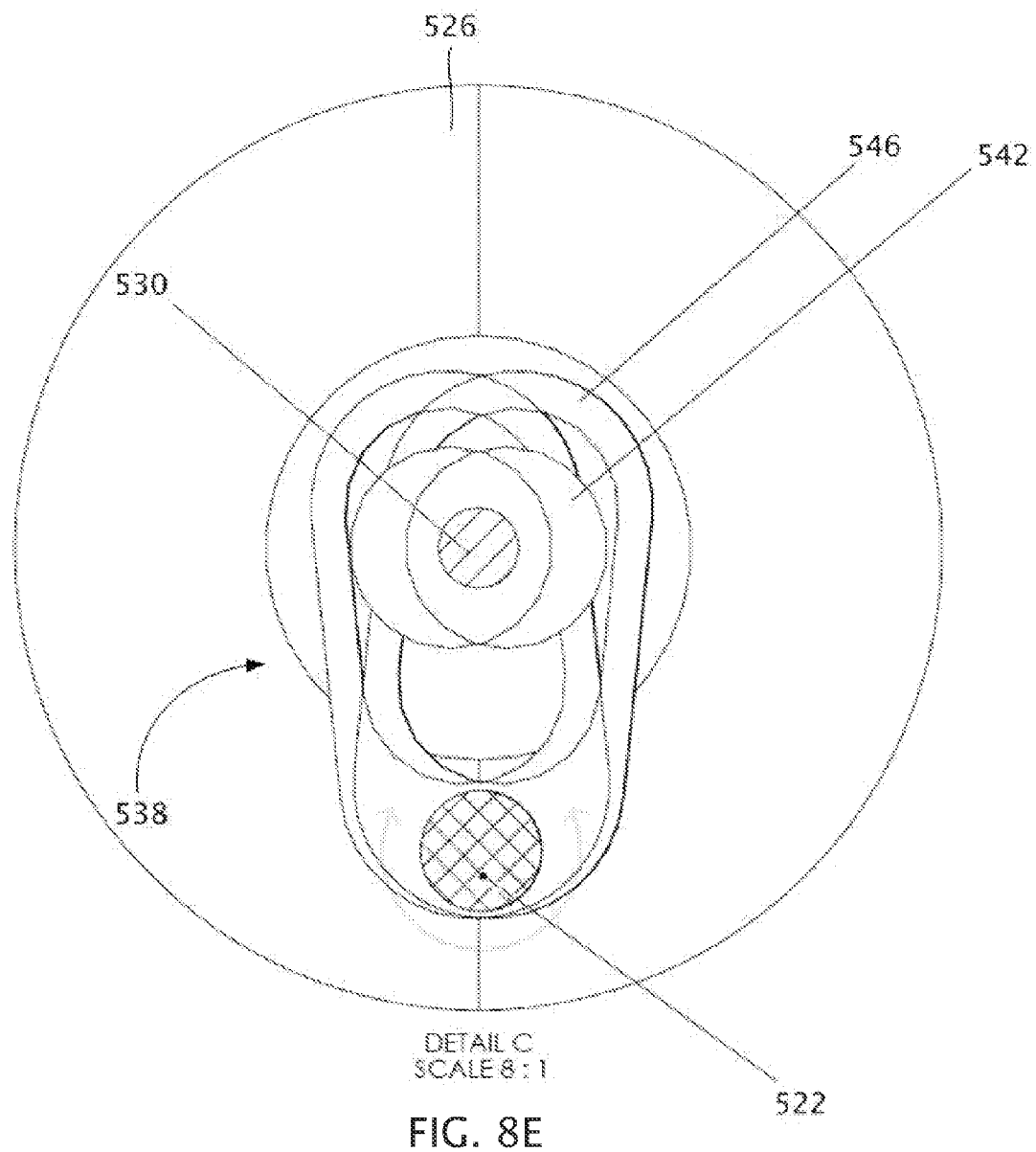
FIG. 8E depicts a cutaway front view of the driver of FIG. 8A.
Figure 8G:
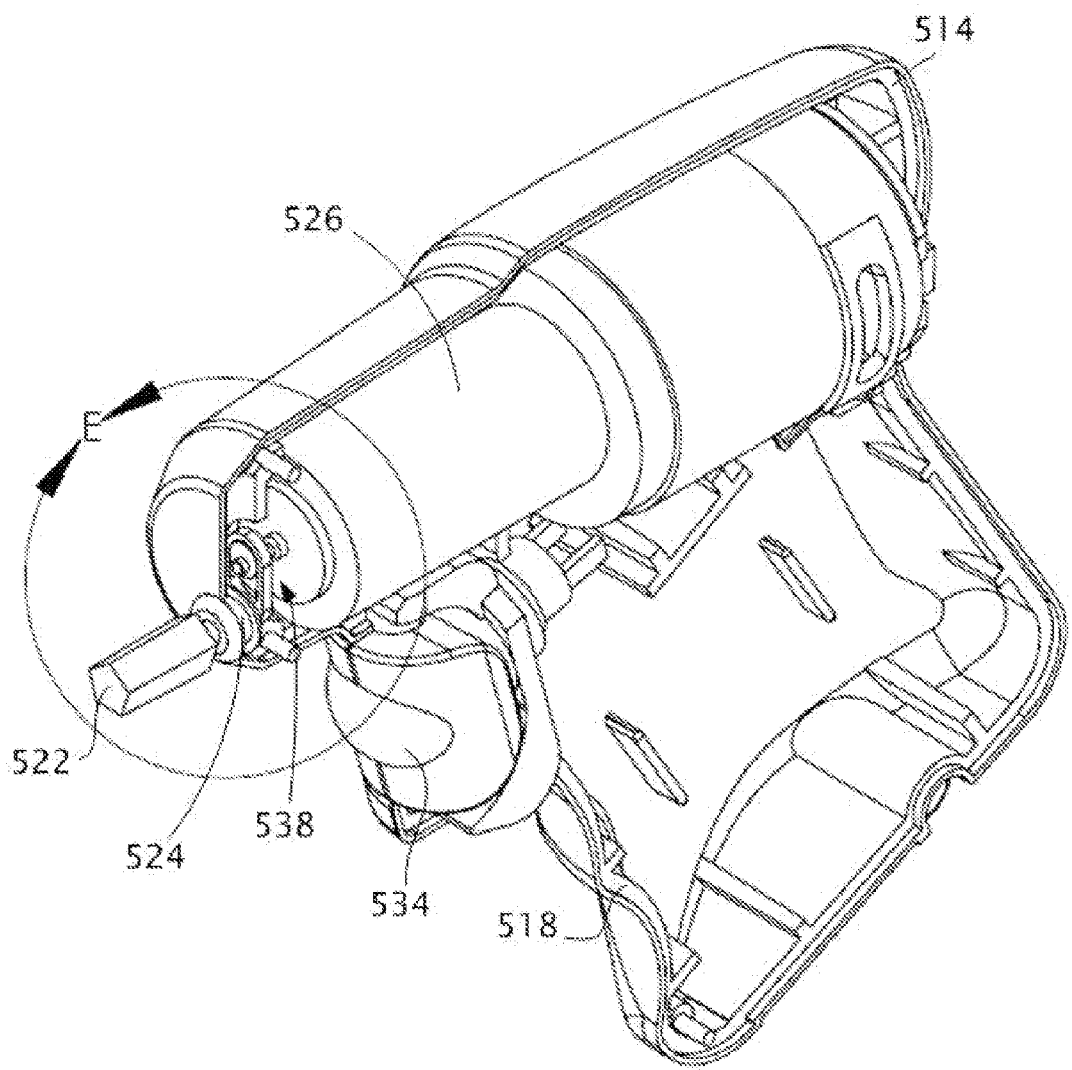
FIG. 8G depicts a cutaway perspective view of the driver of FIG. 8A.
Figure 8H:
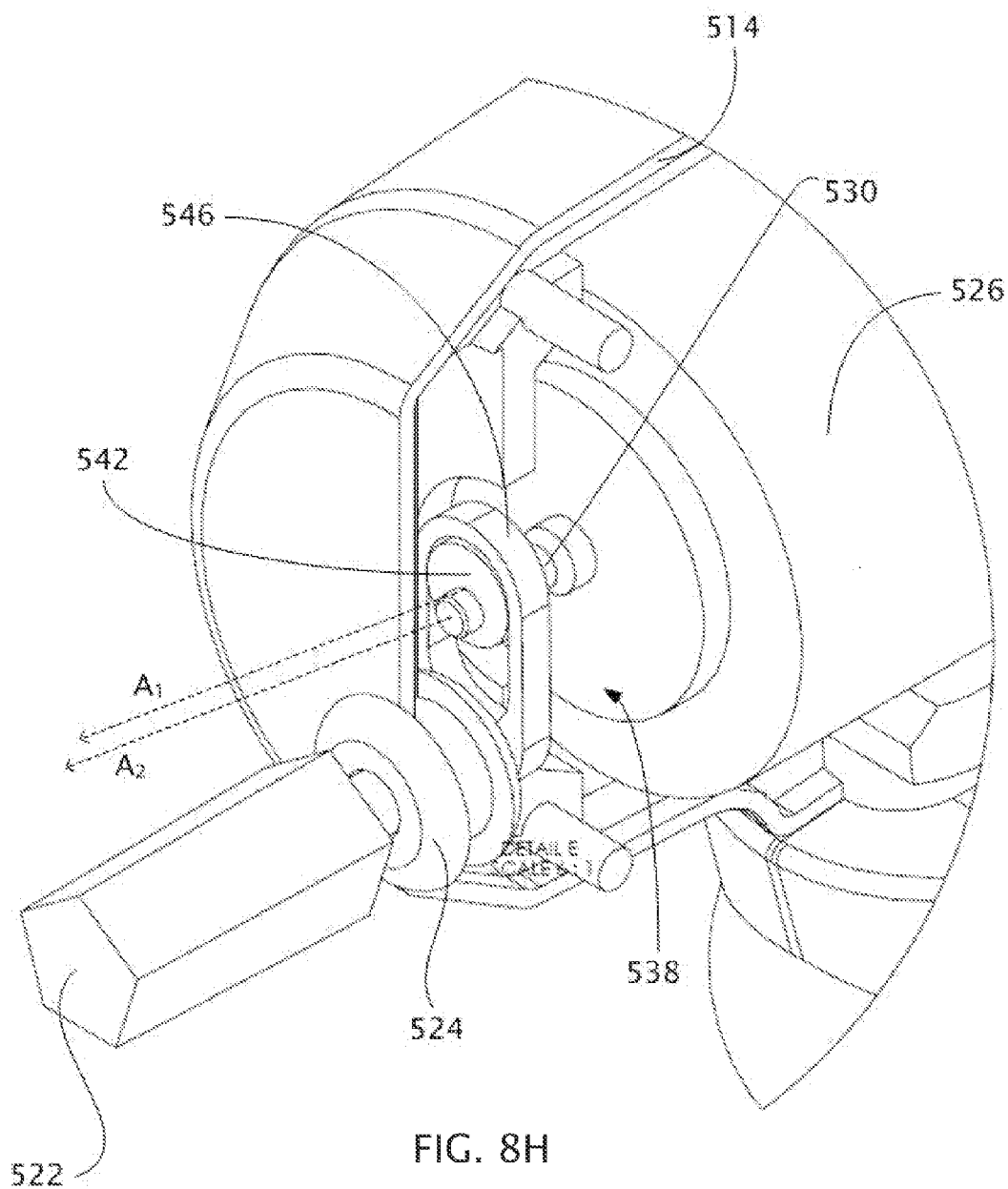
FIG. 8H depicts an enlarged, cutaway perspective view of a portion of the driver of FIG. 8A.

In the embodiment shown, driver 510 comprises a non-geared off-axis drive system 538 configured to couple motor 526 to drive shaft 522. As shown and described in more detail below, in this embodiment, the non-geared off-axis drive system is a drive system that operates to cause reciprocating rotation of drive shaft 522 without needing gears. In other embodiments, off-axis drive system 538 can comprise one or more gears (e.g., to assist in causing oscillating rotation of drive shaft 522). In the embodiment shown, non-geared off-axis drive system 538 comprises cam 542. In the embodiment shown, cam 542 is generally cylindrical in shape and has a centerpoint through which first axis $A_1$ passes (e.g., as depicted in FIG. 8H). Cam 542 further comprises a bore (e.g., depicted in FIGS. 3-8 with motor shaft 530 extending through the bore). The bore of cam 542 is generally cylindrical in shape and has a centerpoint through which second axis $A_2$ passes. In the embodiment shown, second axis $A_2$ is different than first axis $A_1$, and motor shaft 530 extends through the bore of cam 542 along second axis $A_2$ such that motor 526 can rotate cam 542 about second axis $A_2$. Motor shaft 530 can be secured in fixed relation to cam 542 (e.g., by ball detents, adhesives, threads, and the like). When second axis $A_2$ is different than (e.g., spaced apart from) first axis $A_1$ (e.g., as in the embodiment shown), second axis $A_2$ does not pass through the centerpoint of cam 542 (e.g., and thus, cam 542 does not rotate symmetrically (e.g., is configured to rotate asymmetrically) about second axis $A_2$ and/or motor shaft 530 when motor 526 rotates cam 542).

In the embodiment shown, non-geared off-axis drive system 538 further comprises linking device 546, which is coupled to cam 542 and drive shaft 522, as shown. In the embodiment shown, linking device 546 is configured such that when motor 526 rotates cam 542 (e.g., via motor shaft 530), linking device 546 remains in contact with a portion of an outer surface of cam 542. Further, linking device 546 is configured such that a portion of drive shaft 522 can extend through linking device 546 (e.g., linking device 546 can encircle a portion of drive shaft 522 as depicted in FIGS. 8D-8E). When motor 526 rotates cam 542 (e.g., via motor shaft 530), linking device 546 remains in contact with and in fixed relation to the portion of drive shaft 522 to which linking device 546 is coupled (e.g., such that drive shaft 522 can move in fixed relation with the portion of linking device 546 coupled to drive shaft 522). In other embodiments, linking device 546 can contact and/or couple to cam 542 similarly to the way in which linking device 546 contacts and/or couples to drive shaft 522 in the embodiment shown, and vice versa. In other embodiments, linking device 546 can be unitary with drive shaft 522 and/or cam 542 (e.g., formed from a single piece of material or coupled in a way to comprise a single piece of material (e.g., by welding)).

In the embodiment shown, non-geared off-axis drive system 538 is configured to cause oscillating rotation of drive shaft 522. For example, in the embodiment shown, motor 526 and/or motor shaft 530 rotates uni-directionally (e.g., either clockwise or counterclockwise, depending on, for example, the particular model and/or configuration of motor 526). Non-geared off-axis drive system 538 is configured such that the uni-directional rotational motion of motor 526 and/or motor shaft 530 causes bi-directional rotation (e.g., alternating clockwise and counterclockwise rotation) of drive shaft 522 while motor 526 and/or motor shaft 530 rotates uni-directionally. One way of quantifying oscillating rotation, for example, is by a degree (or an arc distance) that an object rotates in one direction (e.g., clockwise) before oscillating to another direction (e.g., counterclockwise). A degree of rotation of drive shaft 522 in a clockwise and counterclockwise direction can vary (e.g., depending on the dimensions of the components of off-axis drive system 538, drive shaft 522, and/or motor shaft 534). For example, in some embodiments, off-axis drive system 538, drive shaft 522, and/or motor shaft 534 can comprise dimensions configured such that drive shaft 522 can rotate equal to or less than 180 degrees (e.g., 180, 150, 120, 90, 60 degrees or less) in one direction (e.g., clockwise) before oscillating in the opposite rotational direction (e.g., counterclockwise). In some embodiments, off-axis drive system 538, drive shaft 522, and/or motor shaft 534 can comprise dimensions configured such that drive shaft 522 can rotate equal to or less than 30 degrees (e.g., 30, 25, 20, 15, 10, 5 degrees or less) in one direction (e.g., clockwise) before oscillating to another direction (e.g., counterclockwise).

Figure 9A:
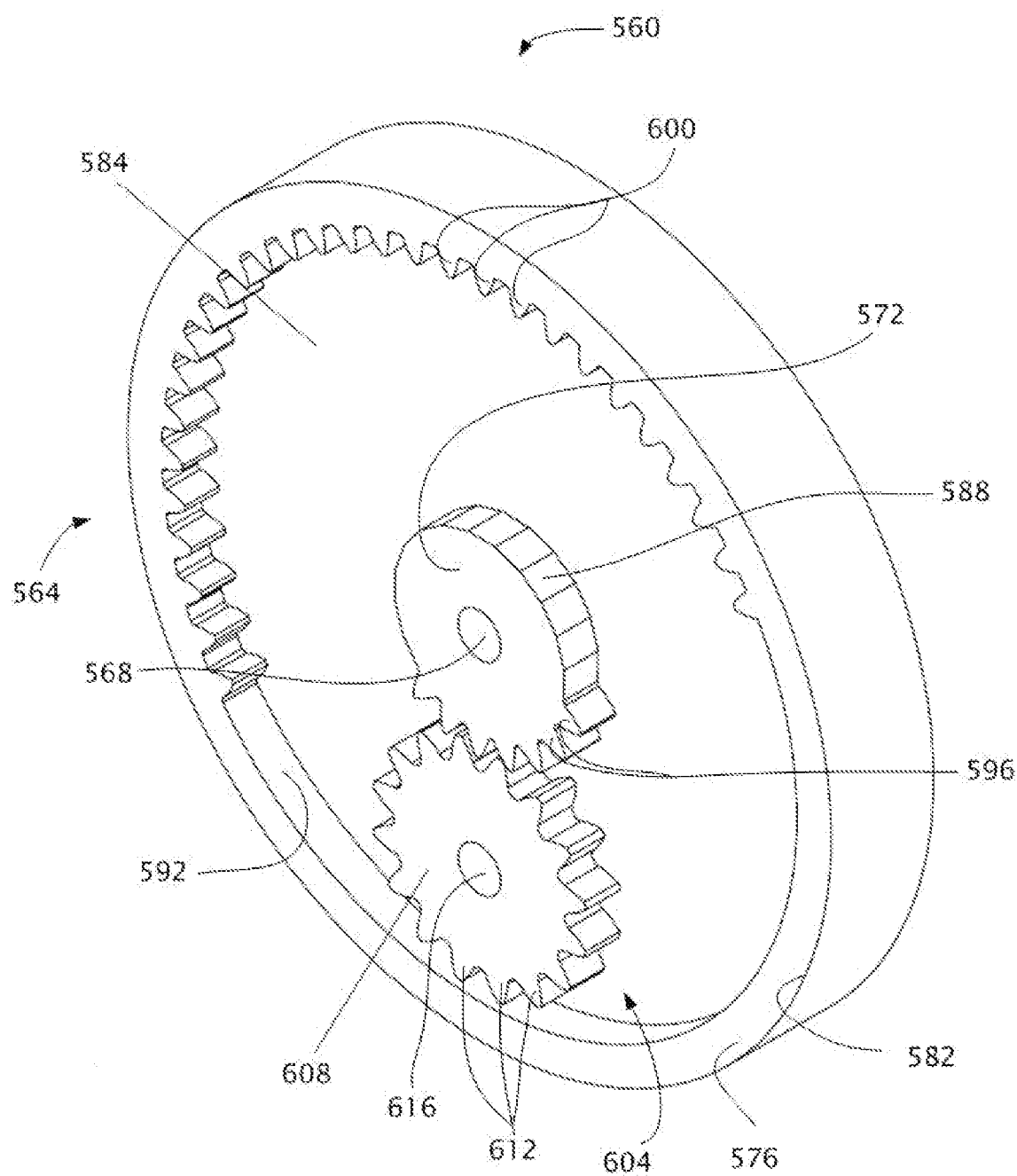
FIG. 9A depicts a perspective view of one embodiment of a multi-gear drive system for some embodiments of the present drivers.
Figure 9B:
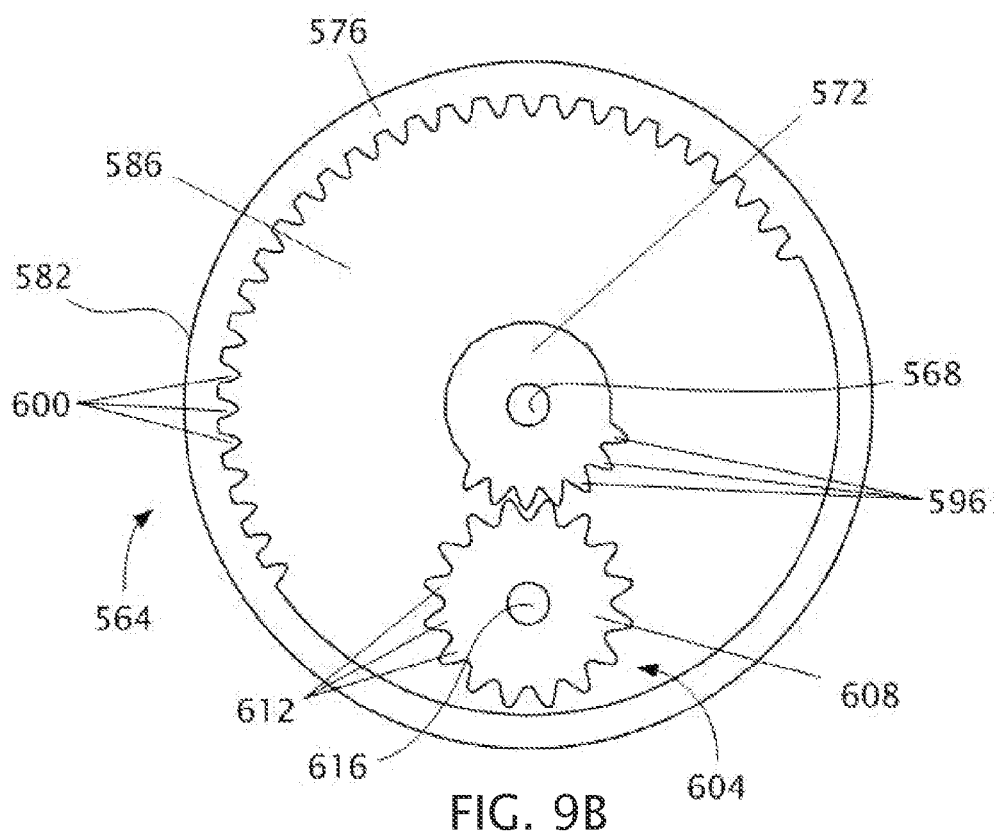
FIGS. 9B-9C depict front views of the multi-gear drive system of FIG. 9A in two states of operation.
Figure 9C:
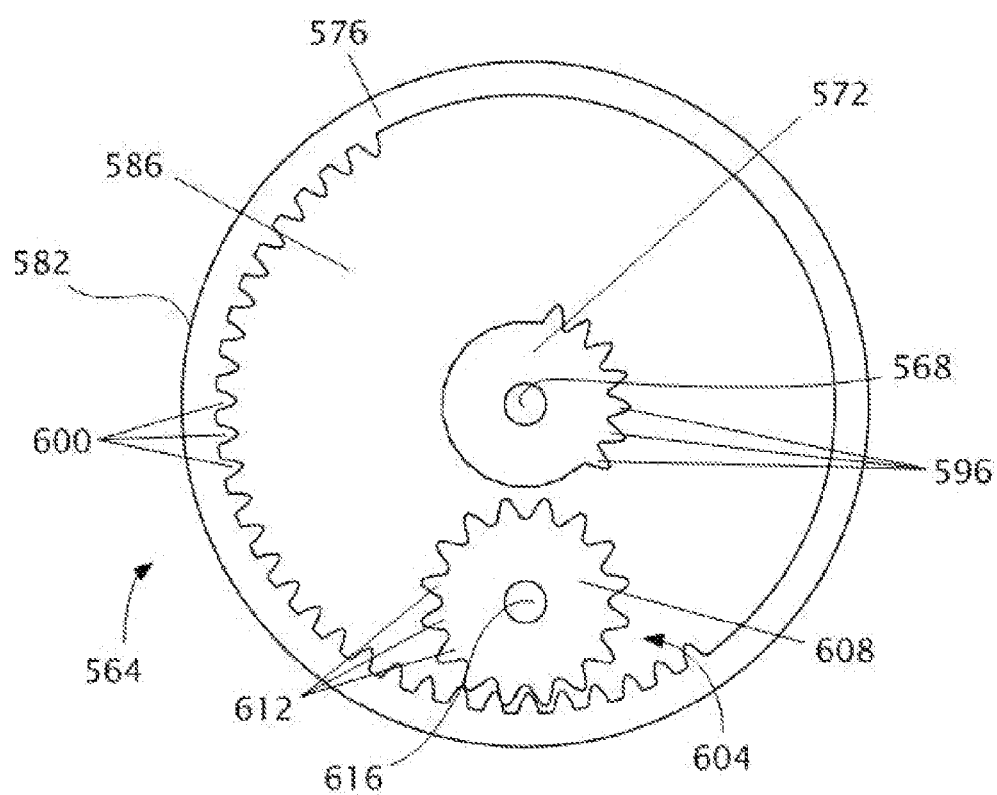

Referring now to FIGS. 9A-9C, designated by the reference numeral 560 is another embodiment of a drive system (e.g., a multi-gear drive system) configured to cause oscillating rotation of drive shaft 522 (as described in detail above). Multi-gear drive system 560 is configured to couple motor 526 (e.g., motor shaft 530) to drive shaft 522. In the embodiment shown, motor 526 is coupled in fixed relation to at least one gear of the multi-gear drive system 560. Multi-gear drive system 560 comprises first gear 564. First gear 564 has first bore 568 configured such that motor 526 (e.g., motor shaft 530) can extend through first bore 568 to rotate first gear 564. In some embodiments, motor 526 (e.g., motor shaft 530) can be coupled (e.g., in fixed relation) to first gear 564 (e.g., via ball detents, adhesives, threads, and/or the like); and in other embodiments, motor 526 (e.g., motor shaft 530) can be unitary with first gear 564 (e.g., formed from a single piece of material or configured to comprise a single piece of material (e.g., by welding)). In the embodiment shown, first gear 564 has first surface 572 extending radially outward from first bore 568. First gear 564 also has second surface 576 extending radially inward from outer edge 580 of first gear 564. Further, first gear 564 has third surface 584 between first surface 572 and second surface 576. Third surface 584 is recessed with respect to first surface 572 and second surface 576, forming an inner wall 588 adjacent to first surface 572 and an outer wall 592 adjacent to second surface 576 (e.g., an intersection of first surface 572 and third surface 584 defines inner wall 588, and an intersection of second surface 576 and third surface 584 defines outer wall 592).

In the embodiment shown, inner wall 588 is—but is not required to be—substantially perpendicular to first surface 572 and third surface 584; and, similarly, outer wall 592 is—but is not required to be—substantially perpendicular to second surface 576 and third surface 584. Further, in the embodiment shown, inner wall 588 comprises a first height extending (the shortest distance) from third surface 584 to first surface 572, and outer wall 592 comprises a second height extending (the shortest distance) from third surface 584 to second surface 576. In the embodiment shown, the first height of inner wall 588 is substantially equal to the second height of outer wall 592. In other embodiments, first height of inner wall 588 and second height of outer wall 592 may differ (e.g., depending on a desired angle of a second gear (discussed in detail below) with respect to first gear 564). In the embodiment shown, the outer perimeter of first surface 572 and inner wall 588 define a generally circular, cylindrical outer surface, and the inner perimeter of second surface 576 and outer wall 592 define a generally circular, cylindrical inner surface. In the embodiment shown, a portion of inner wall 588 of first gear 564 defines a plurality of teeth 596. In the embodiment shown, less than 50 percent (e.g., between 30 and 40 percent) of the circumference defined by inner wall 588 comprises plurality of teeth 596 (e.g., the portion of inner wall 588 with teeth 596 has an angular span of less than 180 degrees, such as, for example, between 110 and 145 degrees). In other embodiments, 50 or more percent of inner wall 588 can comprise plurality of teeth 596 (e.g., depending on a direction of rotation of first gear 564, a desired degree of rotation of drive shaft 522, and the like). Further, a portion of outer wall 592 of first gear 564 defines plurality of teeth 600. In the embodiment shown, approximately (e.g., substantially or exactly) 50 percent (e.g., between 45 and 55 percent) of the circumference defined by outer wall 592 comprises plurality of teeth 600 (e.g., the portion of outer wall 592 with teeth 600 has an angular span of approximately 180 degrees, substantially or exactly equal to 180 degrees, or between 160 and 200 degrees). In other embodiments, less than 50 percent or more than 50 percent (an angular span of less than 180 degrees or more than 180 degrees) of outer wall 592 can comprise plurality of teeth 600 (e.g., depending on a direction of rotation of first gear 564, a desired degree of rotation of drive shaft 522, and the like).

In the embodiment shown, multi-gear drive system 560 comprises second gear 604. Second gear 604 is disposed adjacent to (e.g., parallel to and with a rotational axis that is perpendicular to) third surface 584 of first gear 564, and between inner wall 588 and outer wall 592. In the embodiment shown, second gear 604 has a height, and extends from third surface 584 of first gear 564 by a distance, substantially equal to first height of inner wall 588 and second height of outer wall 592 (e.g., such that surface 608 of second gear 604 is substantially coplanar with first surface 572 and second surface 576). In other embodiments, second gear 604 can have a height, and extend a distance from third surface 584, that is different from at least one of first height of inner wall 588 and second height of outer wall 592. In the embodiment shown, second gear 604 has a generally circular shape and comprises plurality of teeth 612. Plurality of teeth 612 of second gear 604 are configured to correspond to and/or engage with plurality of teeth 596 of inner wall 588 and plurality of teeth 600 of outer wall 592. In the embodiment shown, second gear 604 has second bore 616. Drive shaft 522 can extend through second bore 616 of or otherwise be coupled in fixed relation to second gear 604 such that second gear 604 can rotate (e.g., indirectly, via first gear 564 and motor 526) drive shaft 522.

In the embodiment shown, plurality of teeth 596 of inner wall 588 and plurality of teeth 600 of outer wall 592 are configured to engage plurality of teeth 612 of second gear 604 at different times (e.g., teeth 612 of second gear 604 are not engaged with teeth 596 of inner wall 588 at the same time as teeth 600 of outer wall 592). As explained above, multi-gear drive system 560 is configured to cause oscillating rotation of drive shaft 522. For example, motor 526 (e.g., motor shaft 530) can be configured to rotate first gear 564 in one direction (e.g., clockwise). When first gear 564 rotates in one direction (e.g., clockwise), teeth 596 of inner wall 588 can engage teeth 612 of second gear 604 such that second gear 604 and drive shaft 522 rotate in a different direction (e.g., counterclockwise) than first gear 564. As first gear 564 continues to rotate (e.g., via motor 526) teeth 596 of inner wall 588 disengage from teeth 612 of second gear 604, and teeth 612 of second gear 604 engage teeth 600 or outer wall 592, causing second gear 604 and drive shaft 522 to rotate in the same direction (e.g., clockwise) as first gear 564 and motor 526. As explained above, the configuration of teeth on inner wall 588, outer wall 592, and/or second gear 604 can be adjusted depending on, for example, desired degree of rotation of drive shaft 522, desired amount of rotation in a given direction, and the like.

One way of quantifying oscillating rotation, for example, is by a degree (or an arc distance) that an object rotates in one direction (e.g., clockwise) before oscillating to another direction (e.g., counterclockwise). A degree of rotation of drive shaft 522 in a clockwise and counterclockwise direction can vary (e.g., depending on the dimensions of the components of multi-gear drive system 560, drive shaft 522, and/or motor shaft 534). For example, in some embodiments, multi-gear drive system 560, drive shaft 522, and/or motor shaft 534 can comprise dimensions configured such that drive shaft 522 can rotate equal to or less than 180 degrees (e.g., 180, 150, 120, 90, 60 degrees or less) in one direction (e.g., clockwise) before oscillating to another direction (e.g., counterclockwise). In some embodiments, multi-gear drive system 560, drive shaft 522, and/or motor shaft 534 can comprise dimensions configured such that drive shaft 522 can rotate equal to or less than 30 degrees (e.g., 30, 25, 20, 15, 10, 5 degrees or less) in one direction (e.g., clockwise) before oscillating to another direction (e.g., counterclockwise).

Referring now to FIGS. 10A-10H, designated by the reference numeral 710 is another embodiment of the present drivers. Embodiments of driver 710 can comprise—but are not required to comprise—one or more components and/or characteristics of any of the other drivers described and depicted throughout this disclosure (e.g., FIG. 2, FIG. 8A, etc.). In the embodiment shown, driver 710 comprises housing 714, which has a configuration similar to a pistol (e.g., having a barrel-shaped primary portion and a handle extending at a fixed angle relative to the primary portion). Various components (e.g., a motor assembly) associated with driver 710 can be disposed, at least partially, within housing 714. Housing 714 can comprise substantially rigid polymeric material (e.g., a polycarbonate) and, in some embodiments, housing 714 can comprise a single piece of material or more than one piece of material (e.g., two halves coupled with a fluid tight seal). In the embodiment shown, housing 714 includes handle 718, which can have various configurations, including, for example, being configured to be gripped by the hand of a user. In the embodiment shown, handle 718 has opening 722 configured to receive a device (e.g., container 726) containing and/or releasing a pressurized gas (e.g., air, inert gases, nitrogen, and the like). A device (e.g., container 726) containing and/or releasing a gas can be coupled to driver 710 (e.g., threadably, lockably, etc.) within opening 722 of handle 718. Further, a device containing and/or releasing a gas can be configured to release the gas into first passage 730. For example, in the embodiment shown, container 726 comprises container valve 734 configured such that when container 726 is coupled to driver 710 within opening 722 of handle 718, container valve 734 releases or permits the gas to travel from container 726 into first passage 730 (e.g., if the trigger is depressed to permit gas to flow through the motor of the driver, as described below).

In the embodiment shown, driver 710 comprises drive shaft 738. Drive shaft 738 comprises first end 742 configured to be coupled to an intraosseous device (e.g., a needle set), a hub, and/or a coupler assembly and second end 746 configured to be coupled to a motor assembly. In the embodiment shown, first end 742 of drive shaft 738 is a female end having opening 750 (e.g., configured to receive a corresponding male end of an intraosseous device, a hub, and/or a coupler assembly). In the embodiment shown, first end 742 of drive shaft 738 comprises—but is not required to comprise—threads 754 within opening 750 such that first end 742 can be coupled to an intraosseous device, a hub, and/or a coupler assembly with corresponding threads. Drive shaft 738 can also be configured similarly to other embodiments of drive shafts described and depicted throughout this disclosure (e.g., FIG. 2, FIG. 8A, etc.). For example, in some embodiments, drive shaft 738 can have a substantially hexagonal cross-section having a male first end (e.g., corresponding to a coupler assembly (e.g., the coupler assembly depicted in FIG. 6C)). In other embodiments, drive shaft 738 can have a cross-section with any shape configured to be coupled to a corresponding intraosseous device, such as a needle set, a hub, a coupler assembly and/or the like.

In the embodiment shown, drive shaft 738 can be configured to be coupled (e.g., directly or indirectly) to any of the intraosseous devices, hubs, and/or coupler assemblies described in this disclosure, such as a cannula configured to penetrate a target area (e.g., skin, soft tissue, bone, and/or the like). For example, in the embodiment shown, cannula 758 has first end 762, second end 766, and bore 768. Second end 766 is configured to be coupled to driver 710 (e.g., first end 742 of drive shaft 738). First end 762 comprises plurality of tips 770 configured to penetrate a target area. Plurality of tips 770 are configured to penetrate a target area and are formed by an intersection of at least two planar cutting surfaces 774. In other embodiments, first end 762 of cannula 758 can have any suitable end configured to penetrate a target area, such as, for example a plurality of crowns having at least one cutting surface between adjacent crowns (e.g., similarly to the embodiments shown in FIGS. 1B-1D).

In the embodiment shown, drive shaft 738 is coupled to cannula 758 by first hub 778 having first end 782 and second end 786. First end 782 of first hub 778 is configured to be coupled (e.g., securely or removably) to second end 766 of cannula 758. In the embodiment shown, first end 782 of first hub 778 can have depth limiter 790 configured to limit the depth to which cannula 758 can penetrate a target area (e.g., similarly to first hub 140a in FIG. 1A). Second end 786 of first hub 778 is configured to be coupled to drive shaft 738. In the embodiment shown, second end 786 of first hub 778 comprises threads 794 configured to correspond to threads 754 within opening 750 of drive shaft 758. First hub 778 can be configured to be coupled to drive shaft 738 by engaging threads 794 of first hub 778 with threads 754 of drive shaft 738 and rotating first hub 778 in a first direction (e.g., where the first direction corresponds to a direction of rotation of drive shaft 738). However, in other embodiments, first hub 778 can comprise any coupling configuration operable to couple (e.g., directly or indirectly) cannula 758 to drive shaft 738 (e.g., indirectly via a Luer lock fitting configured to be coupled to second hub, as depicted in 150a in FIG. 1A). In other embodiments, first hub 778 can be configured similarly to other hubs described and depicted throughout this disclosure (e.g., first hub 140a, as depicted in FIG. 1A). First hub 778 can further be configured to be coupled to a variety of structures, including, for example, a fluid bag (e.g., an IV fluid bag) and an aspiration device (e.g., a device configured to aspirate a target area). A configuration of first hub 778 can vary depending on the device to which first hub 778 will be coupled, if any.

As with other drivers depicted and discussed throughout this disclosure, driver 710, and more particularly drive shaft 738, can be coupled (e.g., directly or indirectly) to a stylet (or trocar) configured to be disposed in a bore of a cannula (e.g., bore 768 of cannula 758 and also as depicted in FIG. 1A). In some embodiments, a stylet can cooperate with a first end of a cannula (e.g., first end 762 of cannula 758) to define a tip for penetrating a target area (e.g., as shown in the embodiment depicted in FIG. 1C). In some embodiments (e.g., as depicted in FIG. 1C), a first end of a stylet can have at least one tip, at least one first tapered cutting surface extending a first length from the tip, and at least one second tapered cutting surface extending a second length from the tip (e.g., in some embodiments, the first length of the first tapered cutting surface can be less than the second length of the second tapered cutting surface, but is not required to be). In still other embodiments, a first end of a stylet can comprise a surface (e.g., a blunted surface) configured to evacuate a sample from a target area (e.g., located in biological material, such as tissue, bone, bone marrow, etc.) from a bore of a cannula (e.g., bore 768 of cannula 758). Such a stylet can include a second hub (e.g., hub 150a in FIG. 1A), which can be configured to be coupled to drive shaft 738 (e.g., by threads, a Luer lock fitting, and/or the like, permitting the stylet and cannula to rotate in fixed relation to one another, as depicted in FIG. 1A), coupler assemblies (e.g., as depicted in FIG. 4), and/or a first hub of a cannula (e.g., first hub 778 of cannula 758).

In some embodiments, a coupler assembly (e.g., coupler assembly 250a as depicted in FIG. 3) can couple (e.g., directly or indirectly) drive shaft 738 to intraosseous devices (e.g., a cannula, a stylet, etc.), a first hub, and/or a second hub. Examples of coupler assemblies are depicted in FIGS. 3-6C.

In the embodiment shown, driver 710 comprises motor assembly 798. Motor assembly 798 is coupled to drive shaft 738 and is configured to move (e.g., rotate) drive shaft 738 when a gas enters motor assembly 798. In the embodiment shown, motor assembly 798 is—but is not required to be—coupled to drive shaft 738 by gear assembly 802. Gear assembly 802 can be configured, for example, to transfer rotational motion from motor assembly 798 (e.g., from a rotor of motor assembly 798) to drive shaft 738. In the embodiment shown, gear assembly 802 is configured to increase a torque of drive shaft 738 with respect to a torque of motor assembly 798 (e.g., a rotor of motor assembly 798). Further, gear assembly 802 is configured to decrease a rotational velocity of drive shaft 738 with respect to a rotational velocity of motor assembly 798 (e.g., a rotor of motor assembly 798).

Figure 10I:
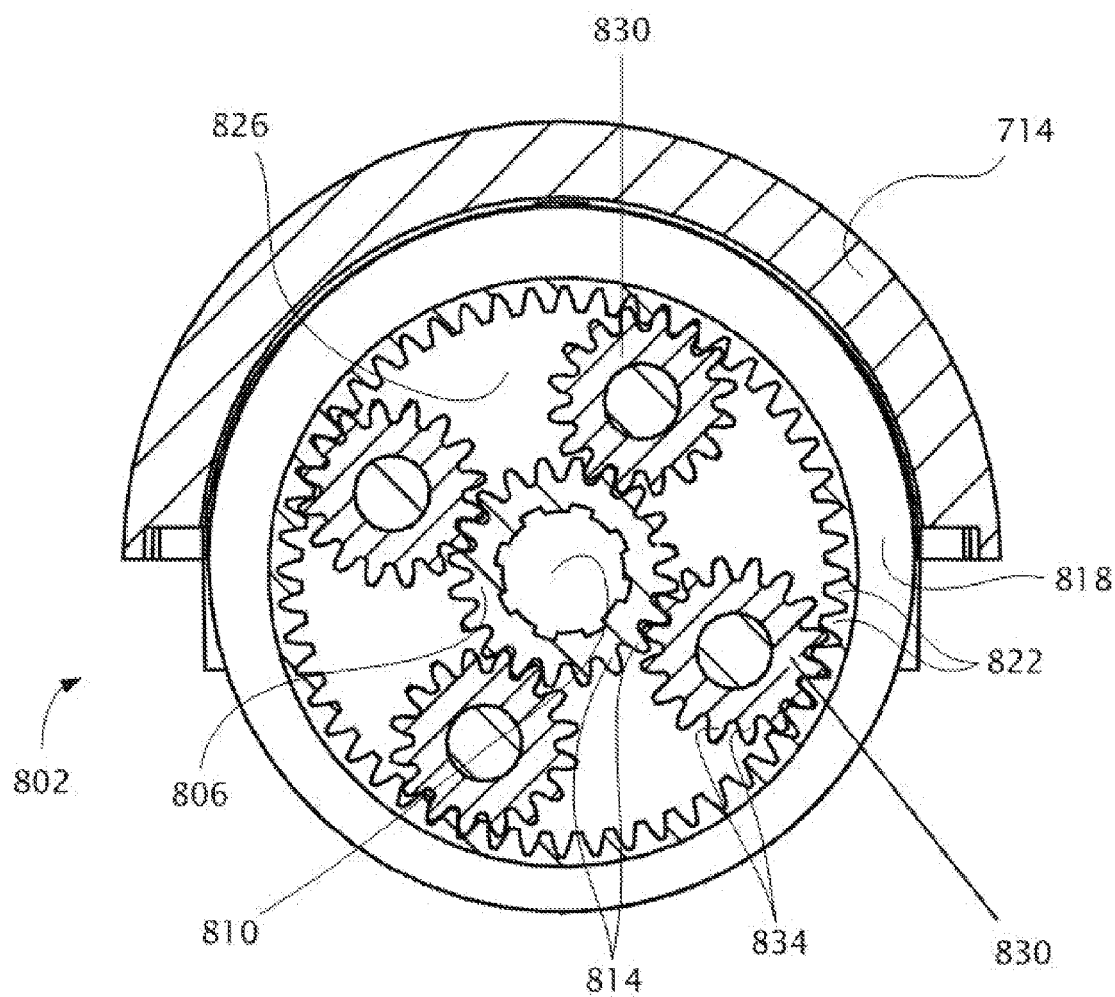
FIG. 10I depicts a cross-sectional view of one embodiment of a gear assembly of the driver of FIG. 10A.
Figure 10J:
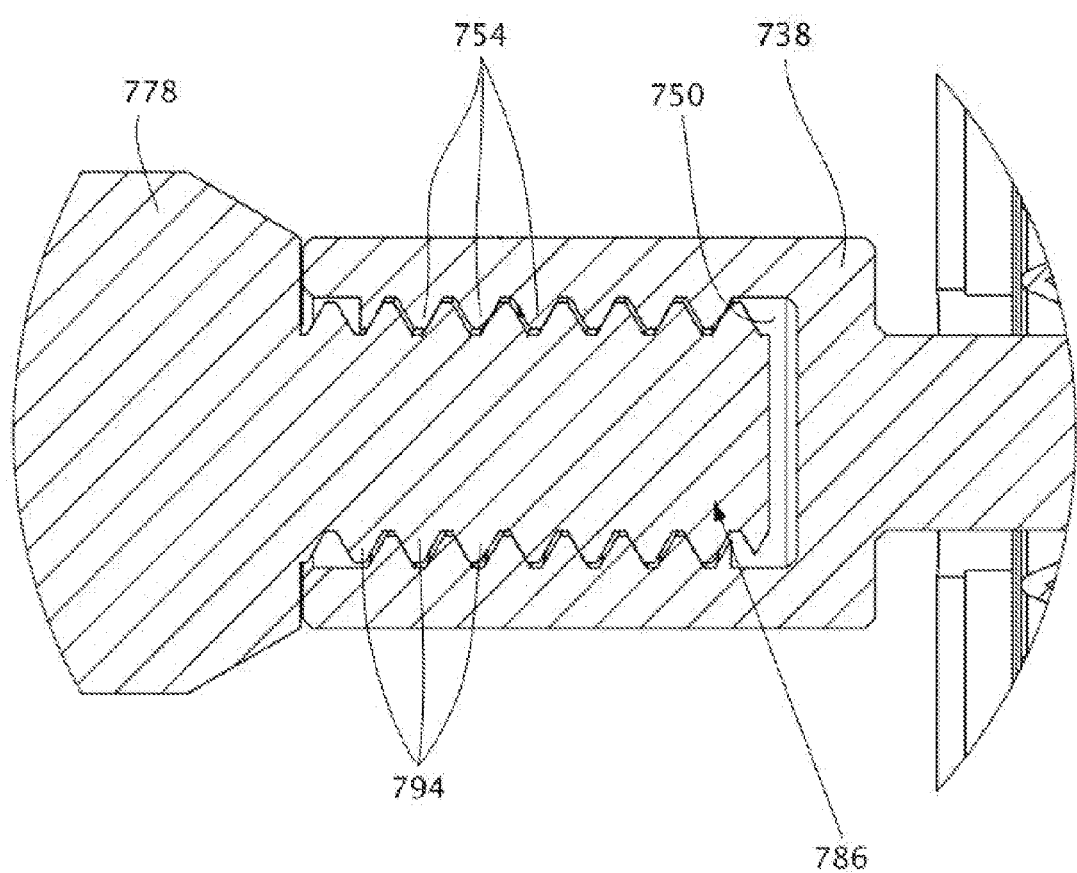
FIG. 10J depicts an enlarged cross-sectional side view of a hub (e.g., of an IO device) coupled to the driver of FIG. 10A.

In the embodiment shown, gear assembly 802 (FIG. 10I) comprises a central inner gear 806 having a central opening or bore 810, plurality of teeth 814, and outer diameter $D_1$. Inner gear 806 is coupled to motor assembly 798 (e.g., to a rotor of motor assembly 798 extending at least partially through opening 810) such that motor assembly 798 can rotate inner gear 806. Gear assembly 802 further comprises an outer (e.g., ring) gear 818 having plurality of teeth 822 and inner diameter $D_2$ (e.g., that is greater than diameter $D_1$). In the embodiment shown, outer gear 818 has opening 826 configured to accommodate inner gear 806 (e.g., such that inner gear 806 is disposed within opening 826 of outer gear 818 and concentric with outer gear 818). In the embodiment shown, plurality of teeth 822 of outer gear 818 are oriented into opening 826 and toward inner gear 806. Outer gear 818 is coupled to drive shaft 738 to permit outer gear 818 to rotate drive shaft 738. In some embodiments, outer gear 818 can be unitary with drive shaft 738 (e.g., such that drive shaft 738 and outer gear 818 are formed of the same piece of material). In the embodiment shown, gear assembly 802 further comprises plurality of planetary gears 830 (e.g., two, three, or more planetary gears) each having plurality of teeth 834. Opening 826 of outer gear 818 is also configured to accommodate plurality of planetary gears 830 (e.g., such that plurality of planetary gears 830 are disposed within opening 826 between outer gear 818 and inner gear 806). Planetary gears 830 are coupled to inner gear 806 and outer gear 818 and configured to transfer rotational motion from inner gear 806 to outer gear 818. For example, motor assembly 798 can rotate inner gear 806 in a first direction. Teeth 814 of inner gear 806 can engage teeth 834 of planetary gears 830 to rotate planetary gears 830 in a second direction, and teeth 834 of planetary gears 830 can further engage teeth 822 of outer gear 818 to rotate outer gear 818 in the second direction (e.g., also moving drive shaft 738 in the second direction).

In the embodiment shown, motor assembly 798 (FIGS. 10E-10H) is configured to move drive shaft 738 when a gas enters motor assembly 798. Motor assembly 798 can comprise, for example, steel, aluminum, stainless steel, and the like. In the embodiment shown, motor assembly 798 comprises rotor housing 838 having first end 842, second end 846, and inner wall 850. Inner wall 850 defines chamber 854 at least partially between first end 842 and second end 846 of rotor housing 838. Rotor housing 838 is configured to have an opening (e.g., opening 858 at second end 846) through which a gas can enter motor assembly 798. Rotor housing also has exhaust channel 860 configured to permit a gas to exit motor assembly 798. In the embodiment shown, motor assembly 798 further includes rotor 862 disposed within chamber 854 of rotor housing 838 and coupled to drive shaft 738 (e.g., via gear assembly 802). Rotor 862 has first end 866 (e.g., corresponding to first end 842 of rotor housing 838), second end 870 (e.g., corresponding to second end 846 of rotor housing 838), and plurality of radial slots 874 extending at least partially between first and second ends 866 and 870 of rotor 862. In the embodiment shown, motor assembly 798 also includes plurality of vanes 878 at least partially disposed within plurality of radial slots 874 and coupled to rotor 862 (e.g., by a spring (e.g., biasing plurality of vanes 878 away from rotor 862)). Plurality of vanes 878 are configured such that when a gas enters motor assembly 798, the gas applies (e.g., as the gas expands) a force to at least a portion of plurality of vanes 878 to move rotor 862. Various gases can be used to move motor assembly 798, including, but not limited to air, nitrogen, and inert gases. Further, gas used with driver 710 can be compressed (e.g., from 50 to 160 pounds per square inch). A gas can apply a sufficient force to plurality of vanes 878 to rotate rotor 862 at, for example, 1 to 50,000 rotations per minute.

In the embodiment shown, rotor housing 838, rotor 862, and plurality of vanes 878 cooperate to form plurality of sub-chambers 882 (e.g., by plurality of vanes 878 extending from rotor 862 to contact rotor housing 838) extending longitudinally with respect to chamber 854 when rotor 862 rotates within chamber 854. For example, when a gas enters motor assembly 798 and moves rotor 862 within chamber 854, rotor housing 838, rotor 862, and plurality of vanes 878 cooperate to vary a volume among adjacent sub-chambers of plurality of sub-chambers 882 to create a pressure gradient (e.g., such that the gas moves plurality of vanes 878 in a direction corresponding to a lower pressure).

In the embodiment shown, driver 710 comprises trigger 886 configured to be engaged to release a gas (e.g., from container 726) into motor assembly 798. Trigger 886 comprises trigger valve 890 configured to release a gas from first passage 730 into second passage 894 when trigger 886 is engaged (e.g., such that first passage 730 and second passage 894 are in fluid communication with motor assembly 798).

Similarly to other embodiments of drivers and intraosseous devices (or components of drivers and intraosseous devices) described in this disclosure, embodiments of the present drivers and drive systems (and components of such drivers and drive systems) depicted from FIGS. 8A-10I can also be included in one or more kits. A kit comprising one or more embodiments (or one or more components) of the present drivers and drive systems can comprise one or more IO devices (or one or more components of IO devices) of any of the kits described in this disclosure (e.g., as depicted in FIGS. 7A-7C). For example, a kit can comprise a driver (e.g., driver 510, driver 710, etc.) and an intraosseous device configured to be coupled to the driver (e.g., a cannula, a stylet, etc.). In some embodiments, a kit can further comprise a coupler configured to couple the driver to the intraosseous needle set. In other embodiments, the kit can comprise an aspiration device configured to be coupled to a cannula. In some embodiments, a kit can comprise at least one sharps protector configured such that at least one intraosseous device can be disposed in the sharps protector to prevent exposure of a cutting surface. In other embodiments, a kit can comprise a containment assembly configured to seal the driver inside the containment assembly to prevent desterilization of at least one of the intraosseous devices and a target area.

The above specification and examples provide a complete description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present drivers, drive systems, and kits are not intended to be limited to the particular forms disclosed. Rather, they include all modifications and alternatives falling within the scope of the claims, and embodiments other than the one shown may include some or all of the features of the depicted embodiment. For example, components may be combined as a unitary structure and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:
1. A driver comprising:
   a drive shaft configured to be coupled to an intraosseous device;
   a motor coupled to a power source and further coupled to the drive shaft by a multi-gear drive system, where the motor is coupled in fixed relation to at least one gear of the multi-gear drive system; and a trigger coupled to the motor and configured to activate the motor to move the drive shaft;

where the multi-gear drive system is configured to cause oscillating rotation of the drive shaft, where the multi-gear drive system comprises a first gear comprising:

a first bore, the motor configured to extend through the first bore to rotate the first gear;

a first surface extending radially outward from the first bore;

a second surface extending radially inward from an outer edge of the first gear; and a third surface between the first and second surfaces and recessed with respect to the first and second surfaces forming an inner wall and an outer wall, where a portion of the inner wall comprises a first plurality of teeth and a portion of the outer wall comprises a second plurality of teeth.

2. The driver of claim 1, where the multi-gear drive system further comprises:

a second gear disposed adjacent to the third surface and between the inner wall and the outer wall, the second gear comprising:

a third plurality of teeth configured to engage the first plurality of teeth of the inner wall and the second plurality of teeth of the outer wall; and a second bore, the drive shaft configured to extend through the second bore such that the second gear can rotate the drive shaft.

3. The driver of claim 2, where the first plurality of teeth of the inner wall and the second plurality of teeth of the outer wall engage the third plurality of teeth of the second gear at different times.

4. The driver of claim 3, where the first plurality of teeth of the inner wall is configured to engage the third plurality of teeth of the second gear such that the second gear rotates in a different direction than when the second plurality of teeth of the outer wall engages the third plurality of teeth of the second gear.

5. The driver of claim 2, where the drive shaft is coupled to the second gear.

6. The driver of claim 2, where the motor is coupled to the first gear.

7. The driver of claim 1, where the inner wall is substantially perpendicular to the first and third surfaces.

8. The driver of claim 1, where the outer wall is substantially perpendicular to the second and third surfaces.

9. The driver of claim 1, where the inner wall comprises a first height extending from the third surface to the first surface and the outer wall comprises a second height extending from the third surface to the second surface.

10. The driver of claim 9, where the first height of the inner wall is substantially equal to the second height of the outer wall are substantially the same.

11. The driver of claim 1, where a range of oscillating rotation of the drive shaft is equal to or less than 30 degrees.

12. The driver of claim 1, where the power source comprises a battery.

13. The driver of claim 1, where the portion of the inner wall that comprises the first plurality of teeth forms less than 50 percent of the inner wall.

14. The driver of claim 13, where the portion of the outer wall that comprises the second plurality of teeth forms approximately 50 percent of the outer wall.

15. The driver of claim 1, where an outer perimeter of the first surface and the inner wall define a cylindrical outer surface.

16. The driver of claim 15, where an inner perimeter of the second surface and the outer wall define a cylindrical inner surface.

17. A driver comprising:

a drive shaft configured to be coupled to an intraosseous device;

a motor coupled to a power source and further coupled to the drive shaft by a multi-gear drive system, where the motor is coupled in fixed relation to at least one gear of the multi-gear drive system; and a trigger coupled to the motor and configured to activate the motor to move the drive shaft;

where the multi-gear drive system is configured to cause oscillating rotation of the drive shaft, where the multi-gear drive system comprises a first gear and a second gear, where at least two separate surfaces of the first gear engage with a surface of the second gear.

18. The driver of claim 17, where the motor is coupled to the first gear and the drive shaft is coupled to the second gear.

19. The driver of claim 17, where the at least two separate surfaces of the first gear comprises:

a first surface comprising a first plurality of teeth; and a second surface comprising a second plurality of teeth, where the surface of the second gear comprises a third plurality of teeth.

* * * * *